(12) United States Patent  
Jabbari

(10) Patent No.: US 9,808,555 B2  
(45) Date of Patent: Nov. 7, 2017

(54) BIOMINERALIZATION PROMOTING MATERIALS AND METHODS OF FORMING SAME

(71) Applicant: University of South Carolina, Columbia, SC (US)

(72) Inventor: Esmaiel Jabbari, Columbia, SC (US)

(73) Assignee: University of South Carolina, Columbia, SC (US)

( * ) Notice: Subject to any disclaimer, the term of this patent is extended or adjusted under 35 U.S.C. 154(b) by 0 days.

(21) Appl. No.: 15/065,084

(22) Filed: Mar. 9, 2016

(65) Prior Publication Data
US 2016/0250379 A1   Sep. 1, 2016

Related U.S. Application Data

(62) Division of application No. 14/260,442, filed on Apr. 24, 2014, now Pat. No. 9,314,549.

(Continued)

(51) Int. Cl.
*A61K 9/70* (2006.01)
*A61L 27/12* (2006.01)
(Continued)

(52) U.S. Cl.
CPC ............... *A61L 27/12* (2013.01); *A61F 2/28* (2013.01); *A61K 9/0024* (2013.01); *A61L 27/18* (2013.01); *A61L 27/227* (2013.01); *A61L 27/50* (2013.01); *A61L 27/54* (2013.01); *A61L 27/56* (2013.01); *A61L 27/58* (2013.01); *B29C 47/0004* (2013.01); *B29C 47/0054* (2013.01);

(Continued)

(58) Field of Classification Search
CPC ........ A61K 9/0024; A61L 27/54; A61L 27/58
See application file for complete search history.

(56) References Cited

U.S. PATENT DOCUMENTS 7,374,774 B2    5/2008  Bowlin et al.
7,531,503 B2 *  5/2009  Atala ................. A61K 41/0042
                                              424/600

(Continued)

OTHER PUBLICATIONS

Park et al; "The Potential of Biomimetic Electrospun-Nanofibrous Scaffolds for Bone Tissue Engineering," Nanofibers, Nov. 14, 2011, pp. 328-345.

*Primary Examiner* — Carlos Azpuru
(74) *Attorney, Agent, or Firm* — Dority & Manning, P.A.

(57) ABSTRACT

Bone tissue biomimetic materials, biomimetic constructs that can be formed with the materials, and methods for forming the materials and constructs are described. The bone tissue biomimetic materials include electrospun nanofibers formed of polymers that are conjugated with peptides that include acidic amino acid residues. The materials can incorporate high levels of mineralization so as to provide mechanical strength and promote osteogenesis and/or osteoconductivity on/in the bone tissue biomimetic materials. The materials and constructs can be utilized in forming tissue engineered structures for in vitro and in vivo use. Macroscopic bone tissue biomimetic scaffolds formed from the materials can be seeded with osteogenic cells and utilized to develop bone graft materials that can exhibit strength and osteoconductivity similar to the native bone and that exhibit uniform distribution of nutrients in the scaffolds.

12 Claims, 10 Drawing Sheets

Related U.S. Application Data

(60) Provisional application No. 61/854,441, filed on Apr. 24, 2013, provisional application No. 61/854,437, filed on Apr. 24, 2013.

(51) Int. Cl.

| | | |
|---|---|---|
| A61L 27/22 | (2006.01) |
| A61L 27/54 | (2006.01) |
| A61K 9/00 | (2006.01) |
| A61L 27/58 | (2006.01) |
| A61L 27/50 | (2006.01) |
| A61L 27/56 | (2006.01) |
| A61F 2/28 | (2006.01) |
| A61L 27/18 | (2006.01) |
| B29C 47/00 | (2006.01) |
| B29C 51/00 | (2006.01) |
| B29C 51/02 | (2006.01) |
| B29C 65/02 | (2006.01) |
| D01D 5/00 | (2006.01) |
| B29K 67/00 | (2006.01) |
| B29K 105/00 | (2006.01) |
| B29L 31/00 | (2006.01) |

(52) U.S. Cl.
CPC ........ *B29C 47/0076* (2013.01); *B29C 51/004* (2013.01); *B29C 51/02* (2013.01); *B29C 65/02* (2013.01); *D01D 5/003* (2013.01); *A61L 2300/112* (2013.01); *A61L 2300/412* (2013.01); *A61L 2400/12* (2013.01); *A61L 2430/02* (2013.01); *B29K 2067/043* (2013.01); *B29K 2067/046* (2013.01); *B29K 2105/0073* (2013.01); *B29K 2105/0088* (2013.01); *B29K 2105/256* (2013.01); *B29K 2995/0056* (2013.01); *B29L 2031/7532* (2013.01); *D01D 5/0076* (2013.01); *D10B 2331/041* (2013.01); *D10B 2401/00* (2013.01); *D10B 2509/00* (2013.01)

(56) References Cited

U.S. PATENT DOCUMENTS

| | | |
|---|---|---|
| 7,737,131 B2 | 6/2010 | Kiick et al. |
| 7,759,082 B2 | 7/2010 | Bowlin et al. |
| 7,767,221 B2 | 8/2010 | Lu et al. |
| 8,066,932 B2 | 11/2011 | Xu |
| 8,071,722 B2 | 12/2011 | Kaplan et al. |
| 8,202,551 B2 | 6/2012 | Li et al. |
| 8,267,992 B2 | 9/2012 | Atanasoska et al. |
| 8,449,622 B2 | 5/2013 | McKay |
| 8,551,390 B2 | 10/2013 | Jun et al. |
| 8,586,345 B2 | 11/2013 | Simpson et al. |
| 8,691,543 B2 | 4/2014 | Gaudette et al. |

\* cited by examiner

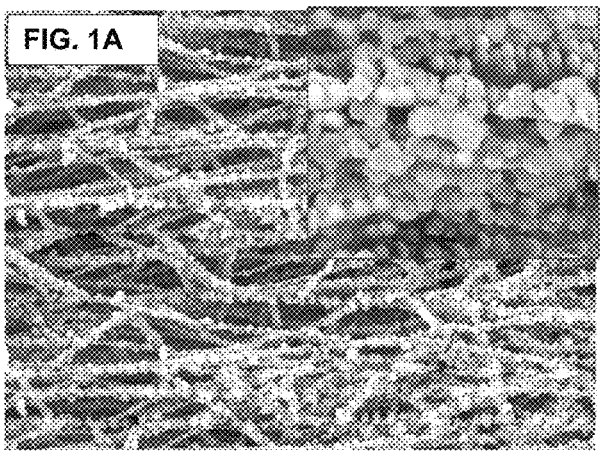
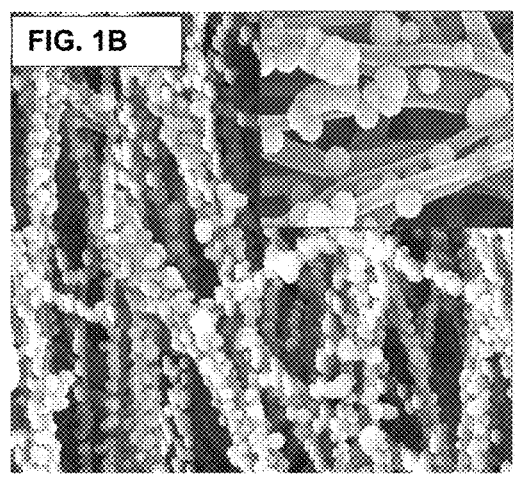
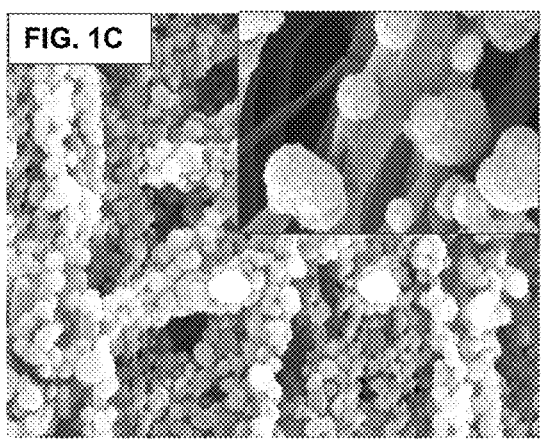

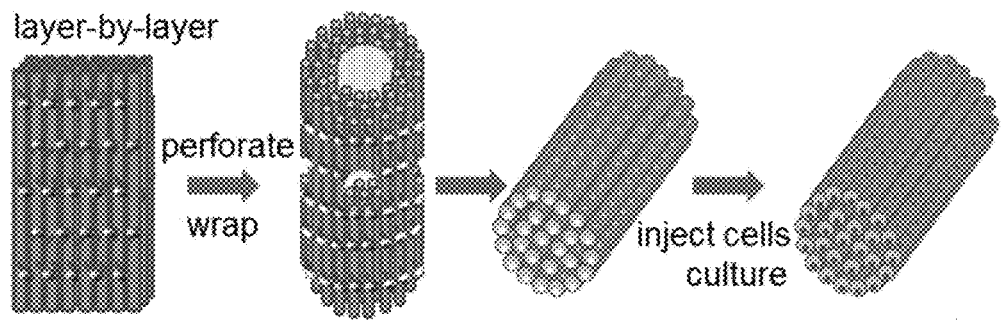
FIG. 2A  FIG. 2B  FIG. 2C  FIG. 2D
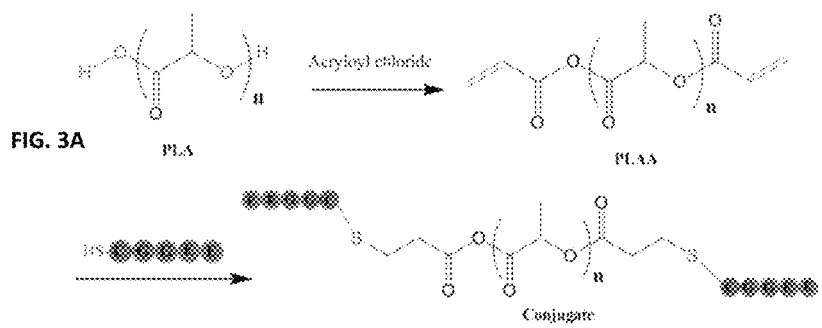
FIG. 3A
FIG. 3B
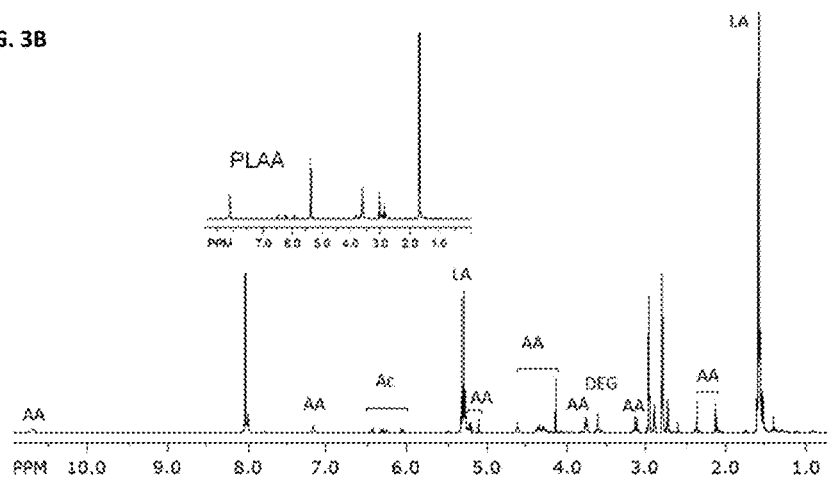

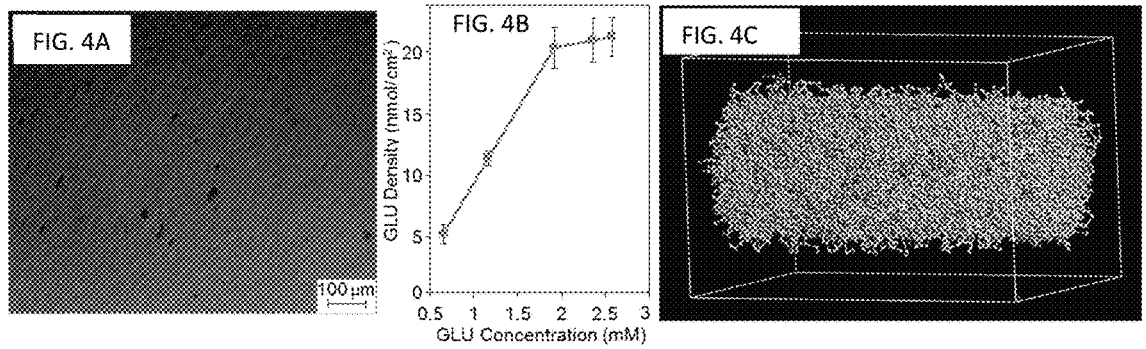
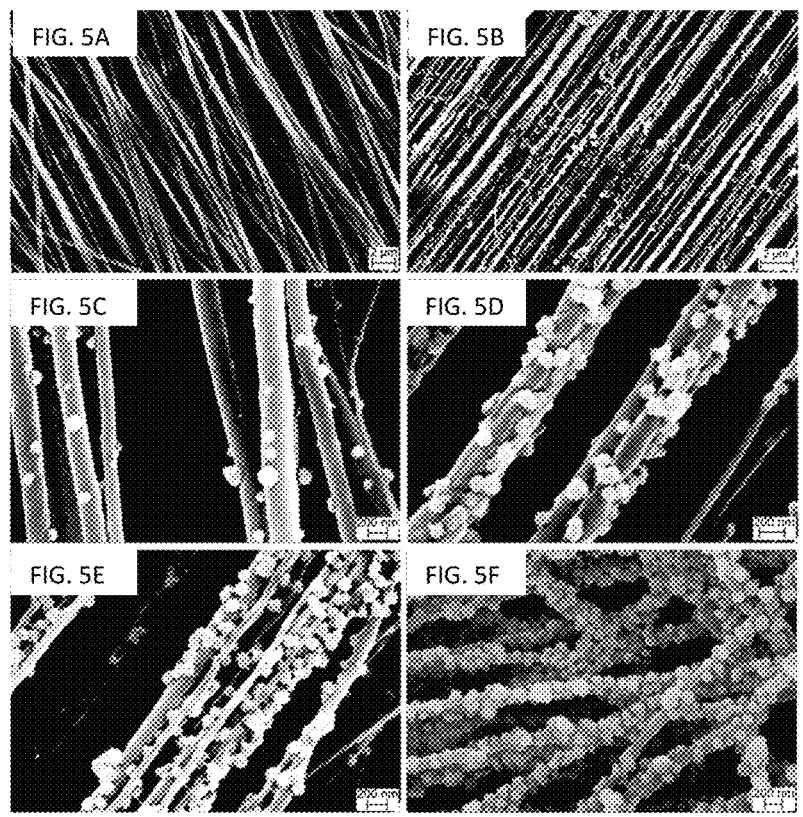

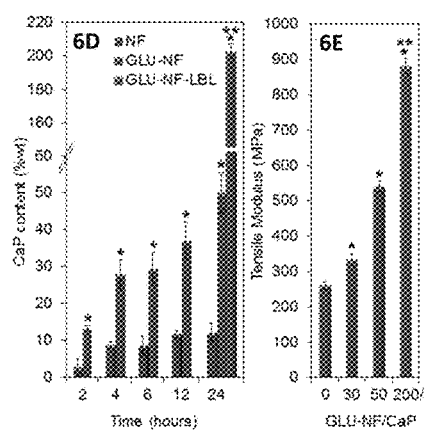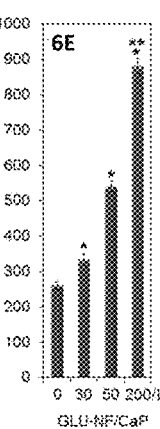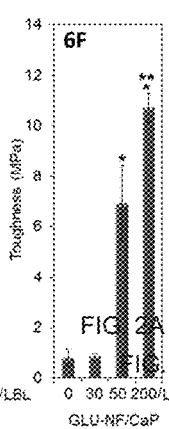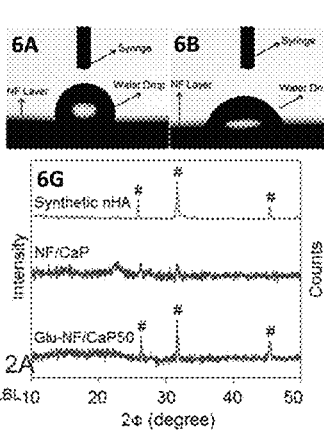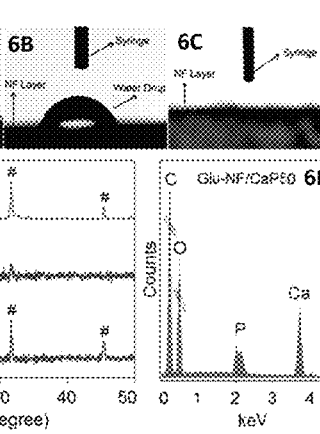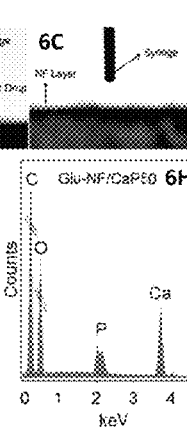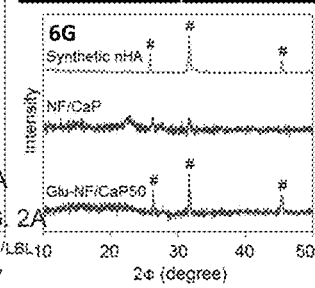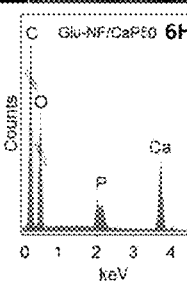
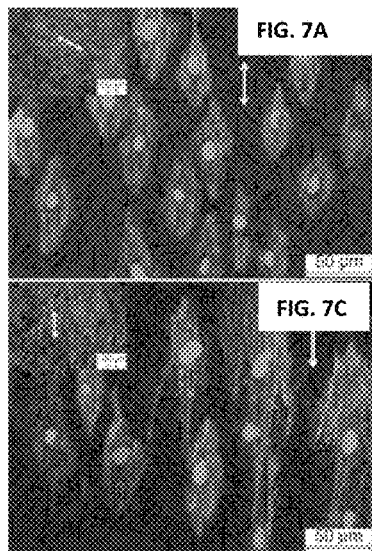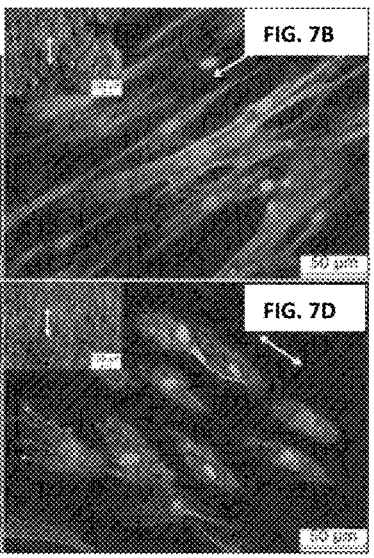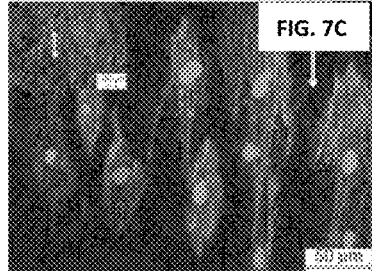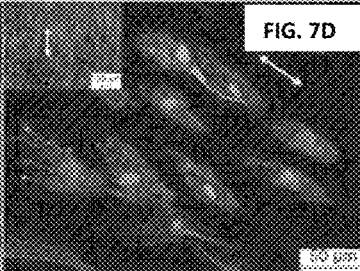

FIG. 8A
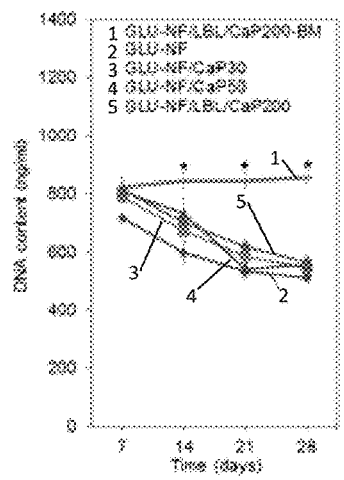
FIG. 8B
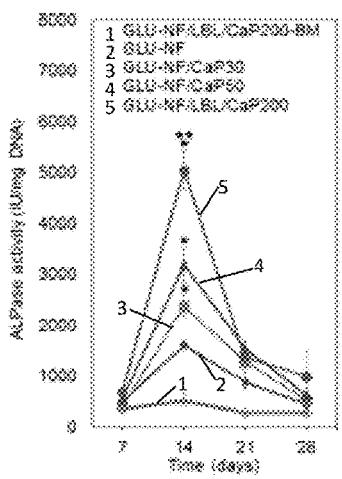
FIG. 8C
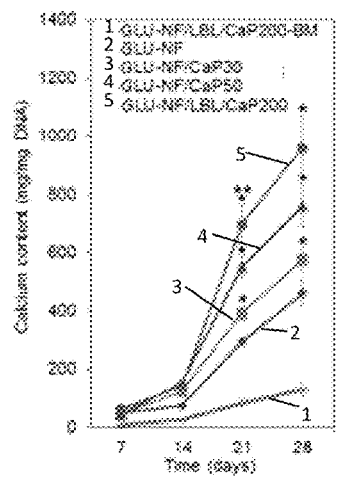
FIG. 9A
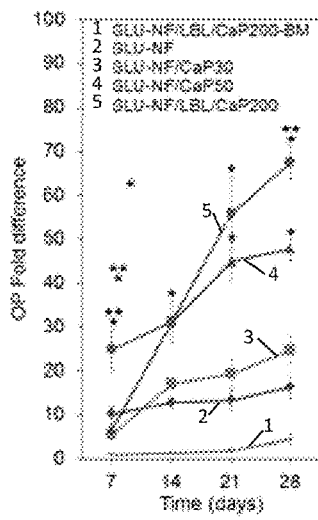
FIG. 9B
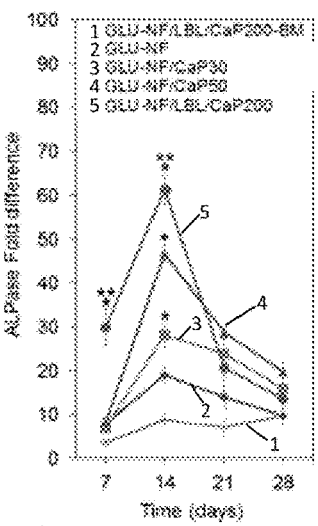
FIG. 9C
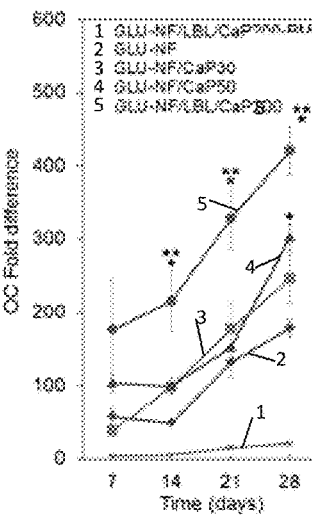
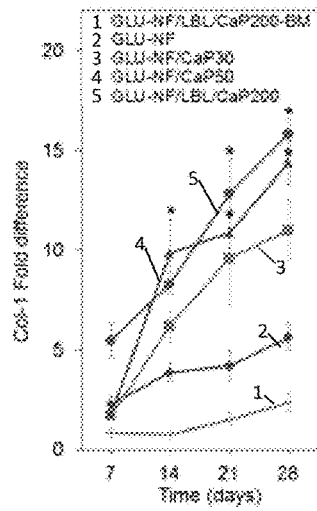
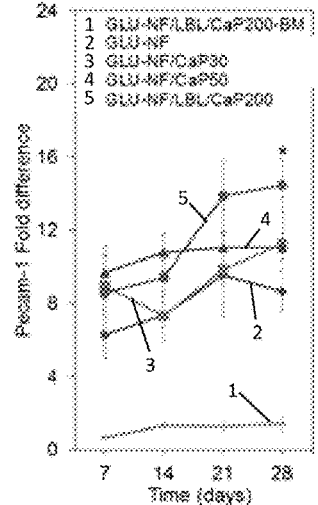
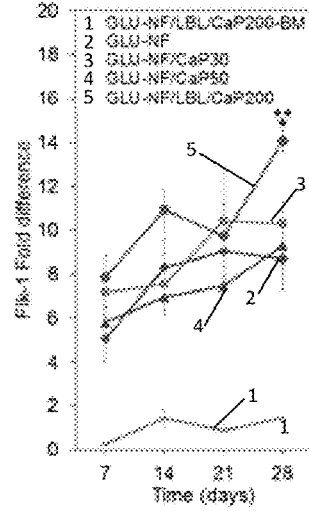
FIG. 9D
FIG. 9E
FIG. 9F

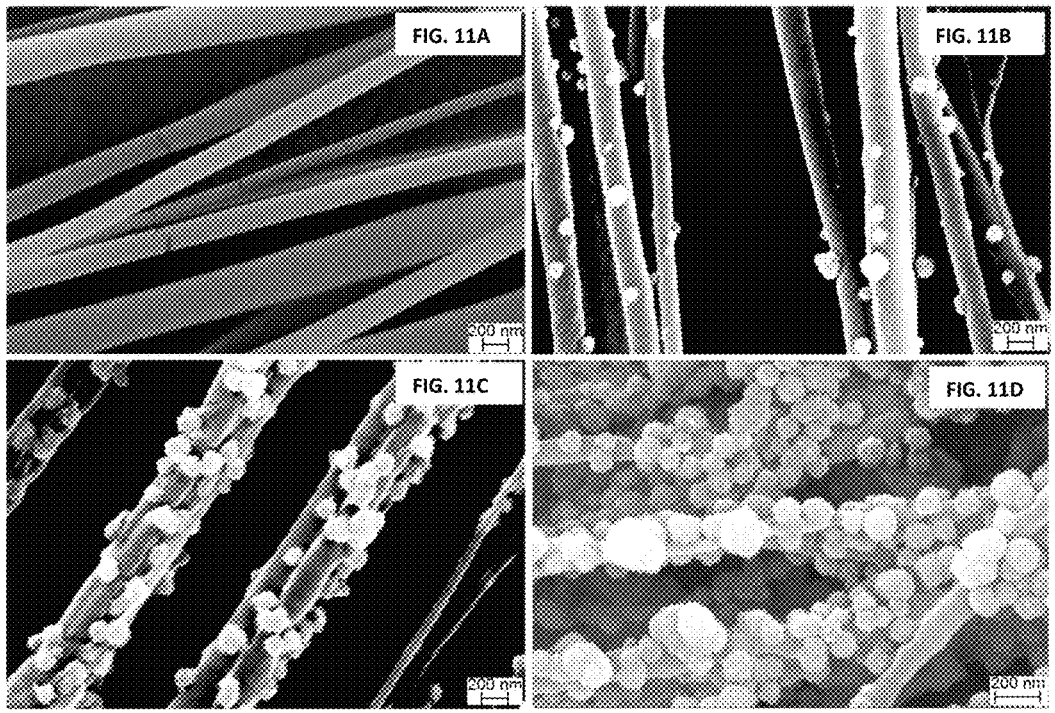
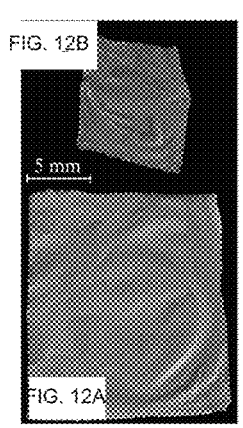
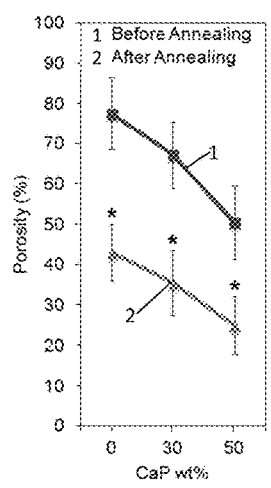
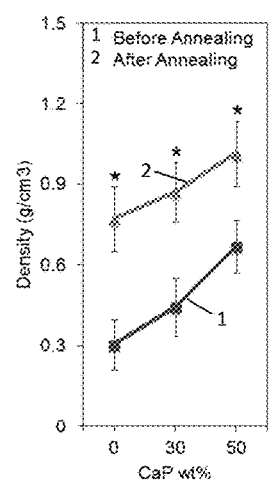
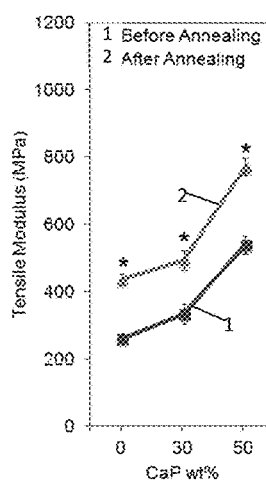

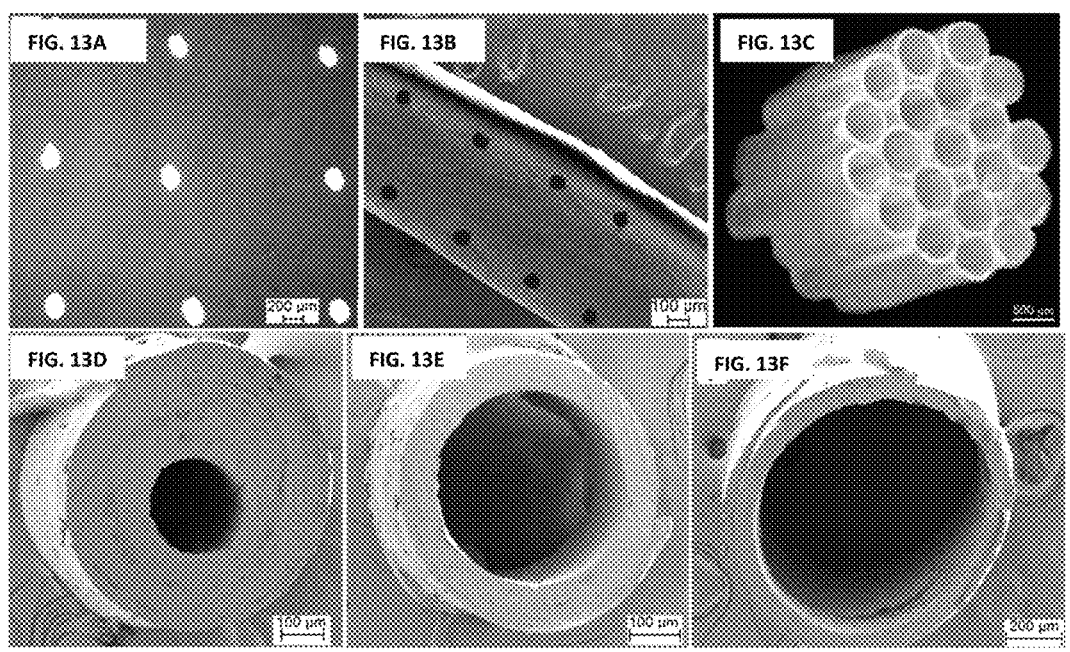

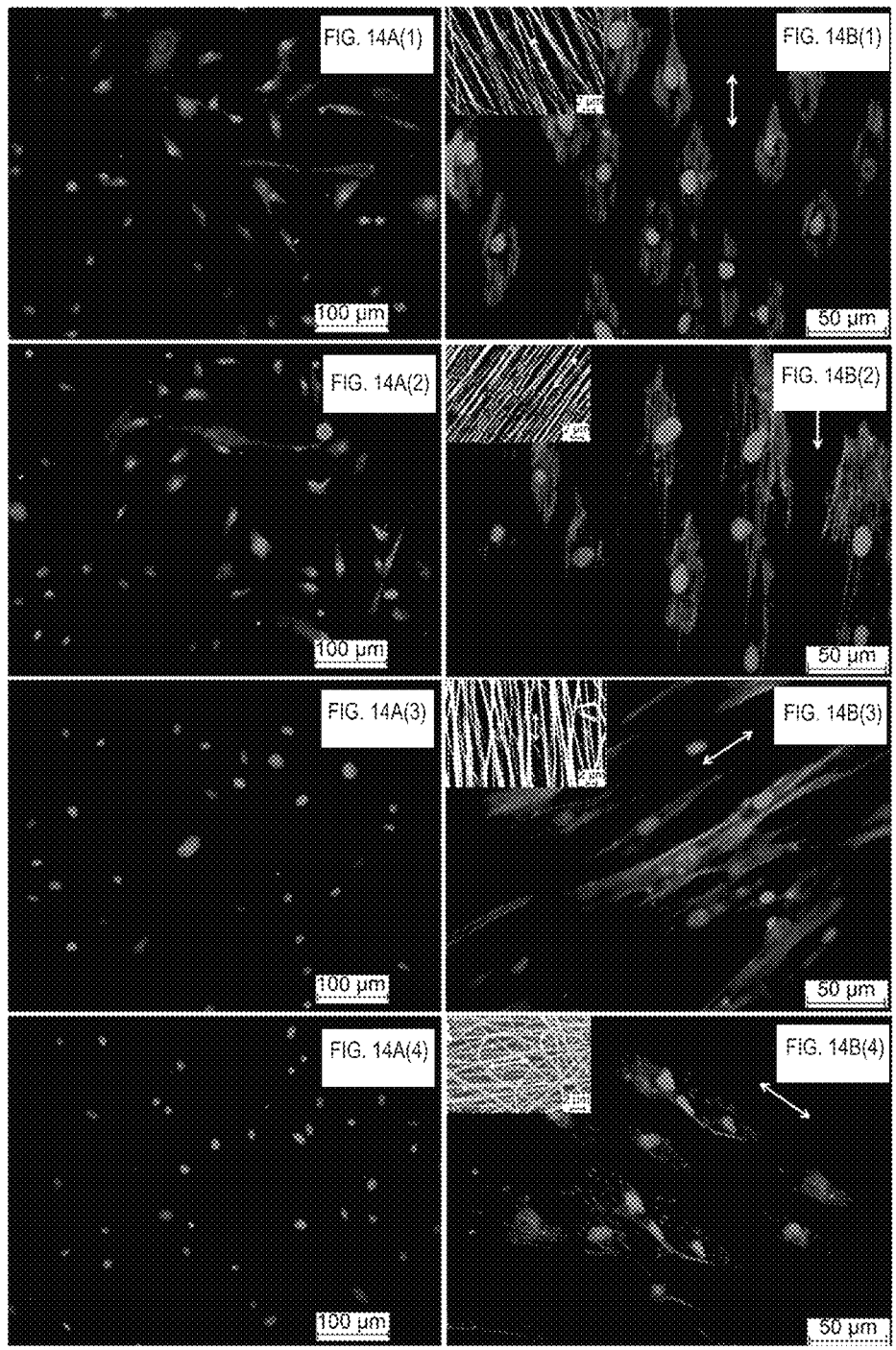

BIOMINERALIZATION PROMOTING MATERIALS AND METHODS OF FORMING SAME

CROSS REFERENCE TO RELATED APPLICATION

This application is a divisional application of U.S. patent application Ser. No. 14/260,442 titled "Biomineralization Promoting Materials and Methods of Forming Same" of Jabbari, filed on Apr. 24, 2014; which claims filing benefit of U.S. Provisional Patent Application Ser. No. 61/854,441 having a filing date of Apr. 24, 2013 titled Effect of Surface Modification of Nanofibers with Glutamic Acid Peptide on CaP Nucleation and Osteogenic Differentiation of Marrow Stromal Cells; and U.S. Provisional Patent Application Ser. No. 61/854,437 having a filing date of Apr. 24, 2013 titled Osteogenic Differentiation of Marrow Stromal Cells (MSCS) in Cortical-Bone-Like Microtubular Structures, all of which are incorporated herein by reference in their entirety.

SEQUENCE LISTING

The instant application contains a Sequence Listing which has been submitted electronically in ASCII format and is hereby incorporated by reference in its entirety. Said ASCII copy, created on Jul. 23, 2014, is named USC-407_SL.txt and is 4,326 bytes in size.

BACKGROUND

Bone is a composite matrix composed of mineralized and aligned collagen nanofibers. Combination of inorganic apatite nanocrystals and organic collagen fibers provides bone with unique mechanical and biological properties. The apatite nanocrystals provide osteoconductivity and compressive strength while the collagen fibers provide elasticity and a template for mineralization and maturation of osteoprogenitor cells. Unique factors that contribute to bone toughness are the aligned network of collagen fibers, apatite nanocrystals, and proteins in the bone extracellular matrix (ECM) that link the apatite crystals to the collagen fibers. On a larger scale, laminated multilayers of calcium phosphate (CaP)-deposited aligned fibers form the cortical bone that is composed of osteons having microtube-like structures surrounding a central micro-canal that provides nutrient/waste transport to and from the bone tissue.

In an effort to mimic the natural morphology at the ECM level, electrospinning has been used to produce aligned nanofibers from natural biopolymers, like collagen and chitosan, or synthetic polymers such as poly(L-lactide) (PLLA) and poly($\epsilon$-Caprolactone) (PCL). Due to their nanoscale size and alignment, electrospun nanofibers provide enormous surface area for cell adhesion, migration, and differentiation, as well as deposition of bioactive agents.

Different methods have been used to create composites of nanofibers reinforced with CaP crystals to improve mechanical strength of the synthetics and provide a conductive matrix for osteoprogenitor cells. In one approach, CaP nanocrystals were mixed with the spinning solution and the solution was electrospun to form CaP composite nanofibers. In that approach, CaP loading and strength of the composite were limited by viscosity of the spinning solution. In another approach, electrospun nanofibers were laminated with a CaP paste to form a composite sheet. This approach was limited to use of the CaP paste however, and toughness of the composite depended on the extent of penetration of the paste into the fiber mesh. In a biomimetic approach, nanofibers were coated with CaP crystals by incubation in a modified simulated body fluid (SBF). This approach mimicked the morphology of the mineralized bone matrix but drawbacks included diffusion-limited penetration of calcium and phosphate ions in the central part of the fiber sheet and lack of crystal nucleation from the fiber surface as opposed to crystal nucleation in solution followed by deposition on the fiber surface. In another approach, a continuous uninterrupted layer of CaP crystals was deposited on the surface of nanofibers within an electric field. This approach produced CaP coated nanofibers at high deposition rate and CaP to fiber ratios exceeding 250% but the CaP layer was continuous and the CaP crystals were not covalently attached to the fiber surface.

What is needed in the art is a method for developing composites that are more accurate bone tissue biomimetics with high stiffness and interconnected microtubular structures to support the exchange of nutrients and oxygen. Ideally, these ECM-level biomimetics can then be used to create larger scale bone graft materials.

Cranial, maxillofacial, oral fractures and large bone defects are currently being treated by using auto- and allografts. Unfortunately, these grafts have limitations in clinical usage such as immune response, donor-site morbidity, and lack of availability. As a result, interest in tissue engineering materials and methods for bone graft procedures has rapidly been growing in an attempt to develop engineered bone grafts that can mimic the bone microstructure.

Tissue engineering approaches require a resilient cell supporting scaffold in order to maintain a 3-dimensional substrate for cell growth and development during the formation of bone tissue. The physical configurations of the scaffolds, which mediate the cell-cell and cell-scaffold interactions, exert strong influence on the success of osteogenic processes in vitro. The success of an engineered scaffold mostly depends on how closely the cell-scaffold relationship mimics that of natural tissue in vivo. Nanofiber composites such as those mentioned above have been used in an attempt to fabricate larger osteoinductive and/or osteoconductive scaffolding. Both in vitro and in vivo studies have demonstrated that organic/inorganic composite fibrous scaffolds support attachment, differentiation, and proliferation of osteoblasts or multipotent stromal cells (MSCs) and facilitate bone healing. However, investigations regarding the effect of fibrous composite scaffolds are still limited.

What are needed in the art are bone tissue biomimetic materials and methods that can be utilized to form rigid constructs in tissue engineering applications for the development of three dimensional mineralized and vascularized cellular structures, for instance in the formation of bone tissue biomimetic materials for use in bone graft applications.

SUMMARY

According to one embodiment, disclosed is a bone tissue biomimetic material. The material can include a fibrous sheet that includes nanofibers. More specifically, the nanofibers can include a biocompatible polymer and the biocompatible polymer can be conjugated to a peptide. The peptide can include multiple acidic amino acid residues. For example, the peptide can be derived from a bone extracellular matrix protein. The acidic amino acid residues can include, e.g., glutamic acid and/or aspartic acid.

Methods for forming a bone tissue biomimetic structure are also disclosed that can include wrapping the fibrous sheet around a mold. The mold can have a circular cross section and an axial length. The fibrous sheet can be wrapped around the mold such that it encircles the mold and extends along at least a portion of the axial length of the mold. Upon heat treatment or annealing of the fibrous sheet that can result in the shrinkage and densification of the sheet, the mold can be removed and the fibrous sheet can retain the tubular shape thus formed, thus mimicking the osteons of cortical bone. A plurality of the tubular structures can also be bundled together and heat treated to fuse the tubular structures and form a multi-tubular construct, thus mimicking the structure of cortical bone.

BRIEF DESCRIPTION OF THE FIGURES

FIG. 1A presents disk crystal shapes as may be nucleated on an electrospun nanofiber according to disclosed methods.

FIG. 1B presents cylindrical crystal shapes as may be nucleated on an electrospun nanofiber according to disclosed methods.

FIG. 1C presents spherical crystal shapes as may be nucleated on an electrospun nanofiber according to disclosed methods.

FIG. 2A presents a schematic representation of a multi-layer fibrous sheet as disclosed herein.

FIG. 2B presents the subsequent perforation and rolling of the fibrous sheet to form an osteon-like tubular structure.

FIG. 2C is a cortical bone-like structure formed by fusing a plurality of tubular structures.

FIG. 2D is a cellular scaffold formed by seeding cells on/in the cortical bone-like structure.

FIG. 3A presents a reaction scheme for synthesis of low molecular weight poly(lactide) conjugated with a 2-mer glutamic acid amino acid sequence with glycine (G) spacer and cysteine (C) terminal group (PLA-CGGEE SEQ ID NO: 1) or PLA-GLU).

FIG. 3B is a $^1$H-NMR spectrum of PLA-GLU macromer; the inset in FIG. 3B is NMR spectrum of Ac-PLA without the GLU conjugate. NMR peaks labeled with LA, AA, and Ac represent lactide, amino acid, and acrylate peaks, respectively.

FIG. 4A, is a fluorescent image of FITC conjugated PLA-CKGGEE peptide (SEQ ID NO: 2) (PLA-GLUK. K is lysine amino acid) nanofibers with 20 nmol/cm$^2$ GLUK peptide surface density.

FIG. 4B illustrates the effect of PLA-GLUK peptide concentration in the electrospinning solution on GLUK peptide surface density on aligned nanofibers.

FIG. 4C illustrates the dissipative particle dynamics (DPD) simulation of PLGA/PLA-GLU showing localization of GLU groups (dark) on the surface of nanofibers (light) within the simulation box. Error bars in FIG. 4A and FIG. 4B correspond to mean±1 standard deviation (SD) for n=3.

FIG. 5A through FIG. 5F present scanning electron microscopy (SEM) images of microsheets after incubation in the simulated body fluid with 10-fold higher concentration of calcium and phosphate ions (m10SBF medium).

FIG. 5A and FIG. 5B are low magnification images of PLGA (without GLU on the nanofiber surface) and PLGA/PLA-GLU (with GLU on the nanofiber surface) microsheets after incubation in m10SBF for 24 h, respectively.

FIG. 5C, FIG. 5D and FIG. 5E are the images of PLGA/PLA-GLU microsheets after 6, 24, and 48 h incubation in m10SBF, respectively.

FIG. 5F is a PLGA/PLA-GLU microsheet deposited with CaP crystals in a layer-by-layer (LBL) approach. Scale bars in FIGS. 5A and 4B represent 2 μm and scale bars in FIG. 5C, FIG. 5D, FIG. 5E and FIG. 5F represent 200 nm.

Figure 10:
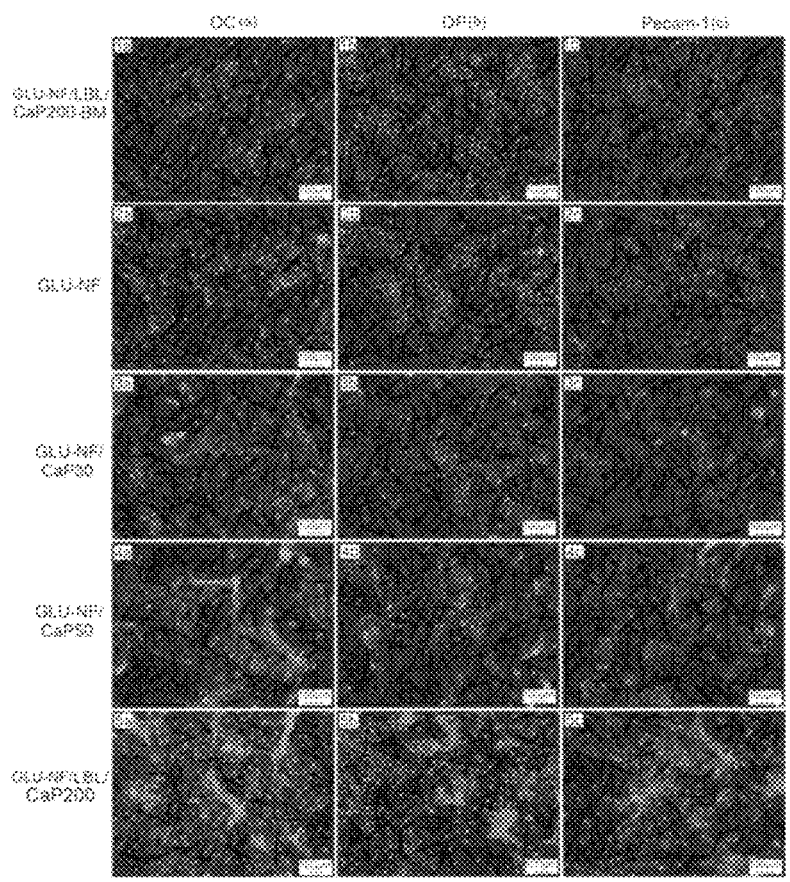

The addition of citric acid changes the crystal shape. The images in FIG. 5A through FIG. 5F show that the CaP crystals are nucleated from the nanofiber surface and they are covalently and firmly attached to the fiber surface. Further, the images show the CaP deposition is in the form of discrete nanoparticles, not as a continuous layer on the fiber surface.

FIG. 6A includes an image of the shape of a water droplet on a PLGA nanofiber microsheet (NF). Also shown is the PLGA/PLA-GLU NF before FIG. 6B and after FIG. 6C incubation in m10SBF. All PLGA/PLA-GLU NF microsheets had zero water contact angle after incubation in m10SBF medium, irrespective of incubation time. The contact angles in FIG. 6A, FIG. 6B, and FIG. 6C were 112±3°, 85±3°, and zero, respectively. At FIG. 6D is illustrated the amount of CaP nucleation and growth (based on the fiber mass) on PLGA fibers without GLU conjugation (NF, 1$^{st}$ bar, 25 μm thick layer) and PLGA/PLA-GLU fibers (GLU-NF, 2$^{nd}$ bar, 25 μm thick layer) with incubation time in m10SBF medium. The 3$^{rd}$ bar in the far left (24 hour) section at 6D is for PLGA/PLA-GLU microsheets produced in a 5-layer LBL approach (each layer 5 μm thick) incubated in m10SBF for 24 h. At FIG. 6E and FIG. 6F are compressive modulus and compressive strength of the PLGA/PLA-GLU fibrous samples as a function of CaP nucleation on the fibers. At FIG. 6G is compared x-ray diffraction spectra of CaP nanocrystals deposited on PLGA NF (NF/CaP, middle) and CaP crystals deposited on PLGA/PLA-GLU microsheets (GLU-NF/CaP50, bottom) after 24 h incubation in m10SBF with that of commercial HA nanocrystals (nHA, top). Peaks centered at 25.8°, 31.8°, and 47° are characteristic diffraction peaks of apatite crystals. FIG. 6H is an EDS spectrum of CaP crystals nucleated and grown on GLU-NF/CaP50 fibers (Ca:P=1.58) very close to the Ca:P ratio of hydroxyapatite. In FIG. 6D one star indicates statistically significant difference (s.d.; p<0.05) between the test group and control (NF in FIG. 6D); two stars indicates s.d. between the multilayer and monolayer GLU-NF/CaP. Error bars correspond to means±1 SD for n=3.

FIG. 7A illustrates the morphology of multipotent stromal cells (MSC) (1500 cells/cm$^2$ initial density) seeded on GLU-NF.

FIG. 7B illustrates the morphology of multipotent stromal cells (MSC) (1500 cells/cm$^2$ initial density) seeded on GLU-NF/CaP30.

FIG. 7C illustrates the morphology of multipotent stromal cells (MSC) (1500 cells/cm$^2$ initial density) seeded on GLU-NF/CaP50

FIG. 7D illustrates the morphology of multipotent stromal cells (MSC) (1500 cells/cm$^2$ initial density) seeded on GLU-NF/CaP200. Each of FIG. 7A-FIG. 7D were on microsheets after two days of incubation in osteogenic medium (scale bar is 50 μm). The inset in each image shows the corresponding image of MSCs seeded on GLU-NF microsheets at 1×10$^5$ cells/cm$^2$ density after 7 days of incubation in osteogenic medium (scale bar in the insets is 100 μm). In the images, cell nuclei and cytoskeletal actin were stained with DAPI and phalloidin. The arrow in the images shows direction of the aligned nanofibers.

FIG. 8A presents the DNA content.

FIG. 8B presents the ALPase activity.

FIG. 8C presents the calcium content of MSCs seeded on GLU-NF/CaP microsheets and incubated in osteogenic medium for up to 28 days. Experimental groups include GLU-NF without incubation in m10SBF (control, 2), GLU-NF/CaP30 (3), GLU-NF/CaP50 (4), and GLU-NF/CaP200 (5) incubated in osteogenic medium. GLU-NF/CaP200-BM group was incubated in basal medium as the negative control. In the figure, one star indicates statistically significant difference (s.d.; $p<0.05$) between the test group and GLU-NF for the same time point; two stars indicate s.d. between the test time point and the previous time in the same group; three stars indicate s.d. between GLU-NF/CaP200 and other GLU-NF/CaP groups for the same time point. Error bars correspond to means±1 SD for n=3.

FIG. 9A (OP) presents mRNA expression levels (as fold difference) of osteopontin FIG. 9B (ALPase) presents alkaline phosphatase.

FIG. 9C (OC) presents osteocalcin.

FIG. 9D (Col-1) presents collagen type-1.

FIG. 9E (Pecam-1) presents platelet endothelial cell adhesion molecule.

FIG. 9F presents Flk-1 for MSCs seeded on GLU-NF/CaP microsheets and incubated in osteogenic medium for up to 28 days. Experimental groups include GLU-NF without incubation in m10SBF (2), GLU-NF/CaP30 (3), GLU-NF/CaP50 (4), and GLU-NF/CaP200 (5). GLU-NF/CaP200-BM group was incubated in basal medium as the negative control. In the figures, one star indicates statistically significant difference (s.d.; $p<0.05$) between the test group and GLU-NF for the same time point; two stars indicate s.d. between the test time point and the previous time in the same group; three stars indicate s.d. between GLU-NF/CaP200 and other GLU-NF/CaP groups for the same time point. Error bars correspond to means±1 SD for n=3.

FIG. 10 presents the expression pattern of osteogenic markers osteocalcin (a, OC, first column), osteopontin (b, OP, second column), and vasculogenic marker Pecam-1 (c, third column) for MSCs seeded on GLU-NF/CaP microsheets after 28 days incubation in osteogenic medium. Experimental groups include GLU-NF without incubation in m10SBF (control), GLU-NF/CaP30, GLU-NF/CaP50, and GLU-NF/LBL/CaP200. Expression pattern of MSCs in GLU-NF/LBL/CaP200-BM negative control group, which was incubated in basal medium, is shown in the first row. Cell nuclei in the images were stained with DAPI.

FIG. 11A is a low magnification SEM image of PLGA microsheets after incubation in m10SBF for 24 h.

FIG. 11B is a low magnification image of PLGA/PLA-GLU microsheets after 6 h incubation in m10SBF.

FIG. 11C is a low magnification image of PLGA/PLA-GLU microsheets after 24 h incubation in m10SBF.

FIG. 11D is a low magnification image of PLGA/PLA-GLU microsheets deposited with CaP crystals in a layer-by-layer (LBL) approach. Scale bars in FIG. 11A-FIG. 11D represent 200 nm.

FIG. 12A presents the shrinkage effect of heat treatment on an aligned nanofiber microsheet before heating.

FIG. 12B presents the shrinkage affect of heat treatment after heating.

FIG. 12C illustrates the effect of heat shrinking on porosity.

FIG. 12D illustrates the effect of heat shrinking on density.

FIG. 12E illustrates the effect of heat shrinking on tensile modulus. Experimental groups included GLU-NF, GLU-NF/CaP30, GLU-NF/CaP50, and GLU-NF/LBL200. One star indicates statistically significant difference (s.d.; $p<0.05$) between before annealing and after annealing for the same experimental group. Error bars correspond to means±1 SD for n=3.

FIG. 13A presents an SEM image of a CaP deposited nanofiber microsheet with an array of circular macropores.

FIG. 13B presents an SEM image of a microtube fabricated by wrapping a perforated microsheet around a needle followed by heat treatment at 80° C. for 10 min.

FIG. 13C is an image of perforated microtube bundles of twenty microtubes with the average microtube diameter of 450 μm.

FIG. 13D is an SEM image of microtubes having an inner diameter of 250 μm

FIG. 13E is an SEM image of microtubes having an inner diameter of 450 μm.

FIG. 13F is an SEM image of microtubes having an inner diameter of 800 μm.

FIG. 14A(1) presents the immunohistochemistry images of MSCs stained with CD73.

FIG. 14A(2) presents the immunohistochemistry images of MSCs stained with CD90.

FIG. 14A(3) presents the immunohistochemistry images of MSCs stained with VE-cadherin.

FIG. 14A(4) presents the immunohistochemistry images of MSCs stained with CD-31.

FIG. 14B(1) illustrates the morphology of MSCs seeded on GLU-NF.

FIG. 14B(2) presents the morphology of MSCs seeded on GLU-NF/CaP30.

FIG. 14B(3) presents the morphology of MSCs seeded on GLU-NF/CaP50.

FIG. 14B(4) presents the morphology of MSCs seeded on GLU-NF/LBL200. Each of FIG. 14A(1)—FIG. 14B(4) show microsheets after seven days of incubation in osteogenic medium (scale bar is 100 μm). In the images, cell nuclei and cytoskeletal actin are stained with DAPI and phalloidin. The arrow in the images shows direction of the aligned nanofibers. The insets show the corresponding SEM images of the GLU conjugated nanofiber microsheets before (GLU-NF, a) and after (GLU-NF/CaP30, b) incubation in m10SBF medium for 6 h and 24 h (GLU-NF/CaP50, c) (scale bar is 2 μm).

Figure 15A:
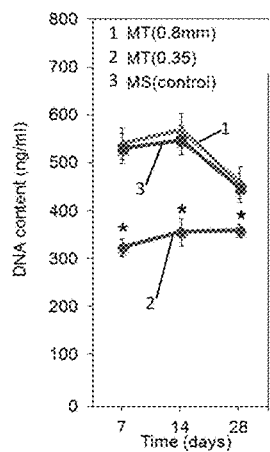

FIG. 15A presents DNA content.

Figure 15B:
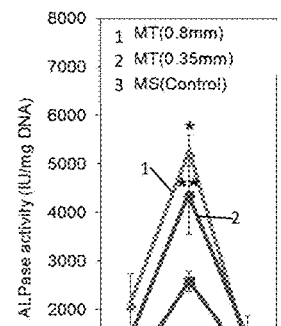

FIG. 15B presents alkaline phosphatase activity.

Figure 15C:
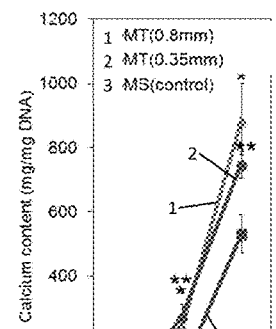

FIG. 15C presents calcium content.

Figure 15D:
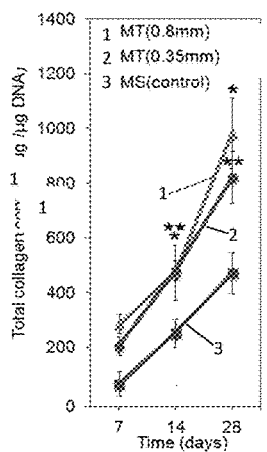

FIG. 15D presents total collagen amount of MSCs seeded inside GLU-NF/CaP50 microtubes and GLU-NF/CaP50 microsheets (control) cultured in osteogenic media. Experimental groups include GLU-NF/CaP50 microsheets (3, control), 0.35 mm microtubes (2), and 0.8 mm diameter microtubes (1). Time points include 7, 14, 28 days. In the figures, one star indicates statistically significant difference (s.d.; $p<0.05$) between 0.35 mm microtubes and microsheets (control) for the same time point and two stars indicates s.d. between 0.8 mm microtubes and microsheets (control) for the same time point. Error bars correspond to means±1 SD for n=3.

Figure 15E:
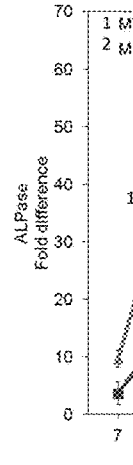

FIG. 15E shows the mRNA expression levels, as fold difference, of Alkaline Phosphatase (ALPase)

Figure 15F:
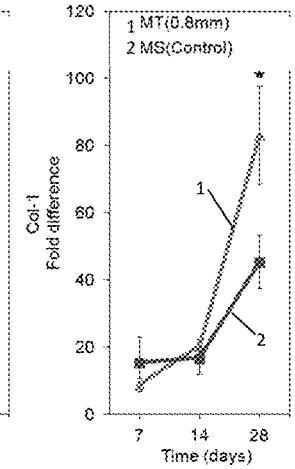

FIG. 15F shows the mRNA expression levels, as fold difference, of collagen type I.

Figure 15G:
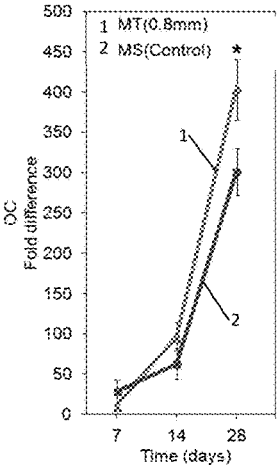

FIG. 15G shows the mRNA expression levels, as fold difference, of OC of MSCs seeded on GLU-NF/CaP50 microsheets (2, control) and inside 0.8 mm diameter microtubes (1) cultured in osteogenic media. In the figures, one star indicates statistically significant difference (s.d.;

p<0.05) between the test group and microsheets (control) for the same time point. Error bars correspond to means±1 SD for n=3.

DETAILED DESCRIPTION

The following description and other modifications and variations to the present invention may be practiced by those of ordinary skill in the art, without departing from the spirit and scope of the present invention. In addition, it should be understood that aspects of the various embodiments may be interchanged both in whole and in part. Furthermore, those of ordinary skill in the art will appreciate that the following description is by way of example only, and is not intended to limit the invention.

In general, the present disclosure is directed to bone tissue biomimetic materials, biomimetic constructs that can be formed with the materials, and methods for forming the materials and constructs. The bone tissue biomimetic materials can incorporate high levels of mineralization so as to promote osteogenesis and/or osteoconductivity on/in the bone tissue biomimetic materials. The disclosed materials and constructs can be utilized in forming tissue engineered structures for in vitro and in vivo use. For instance, macroscopic bone tissue biomimetic scaffolds as disclosed herein can be seeded with osteogenic cells (e.g., osteoblasts or MSC) and utilized to develop bone graft materials that can exhibit little or no immune response or morbidity.

Natural biomineralization is mediated by extracellular matrix (ECM) proteins with amino acid sequences rich in acidic amino acid residues like glutamic acid or aspartic acid. Bone ECM proteins that are rich in acidic residues nucleate CaP crystallization by surface-immobilization on collagen fibrils. For instance, nucleation, growth and stabilization of CaP nanocrystals on collagen fibers in the bone matrix is mediated by ECM non-collagenous proteins such as bone sialoprotein (BSP), osteonectin (ON), osteopontin (OP) and osteocalcin (OC). Glutamic acid (GLU) or aspartic acid sequences ranging from 2-10 residues in these proteins regulate nucleation and growth of CaP crystals on collagen fibers.

The bone tissue biomimetic materials disclosed herein have been designed to emulate the ECM materials through incorporation of acidic amino acid sequences into/on electrospun nanofibers. More specifically, a peptide can be conjugated to a polymer to form a polymer-peptide conjugate, the polymer-peptide conjugate can then be electrospun to form a nanofiber such that a major fraction of the peptide resides on the nanofiber surface. In one embodiment, the polymer-peptide conjugate can be mixed with a second polymer prior to electrospinning. The peptide can include acidic amino acid sequences, similar to the non-collagenous proteins mentioned above. For instance, the peptide can include from 2 to about 10 glutamic acid and/or aspartic acid residues.

The peptide can include other amino acid residues in addition to the acidic amino acid residues. For instance, the sulfhydryl groups of the cysteine residue can be convenient for conjugating the peptide to the polymer and the peptide can therefore include one or more cysteine residues. Other amino acids can be included in the peptide depending upon the utilization of the materials. For instance, the peptide can include a lysine group to facilitate labeling for imaging or quantitative analysis or additional functionalization. The peptide can also include inert amino acids like glycine or alanine to change solubility of the polymer-peptide conjugate in the electrospinning solvent, increase the fraction of peptide on the nanofiber surface, or to increase flexibility of the peptide chain attached to the nanofiber surface.

The peptide can be derived from a natural protein, e.g., a bone extracellular matrix protein or can be a purely synthetic peptide, as desired. For instance, the peptide can be an acidic amino acid rich fragment of a bone ECM protein including, and without limitation to, BSP, ON, OP and OC. The peptide can be formed according to standard practice, for instance by the use of Rink Amide NovaGel™ resin, as is known.

The peptide can be conjugated to the polymer prior to electrospinning the nanofibers. The polymer can be a biocompatible, resorbable polymer and can include (or be processed to include) a functional group that can be utilized to conjugate with the peptide. For instance, if a cysteine residue is to be used for the conjugation reaction, the polymer can include a group such as an acryloyl, a haloacetyl, a maleimides, an aziridine, a vinylsulfone, a pyridyl disulfide, or any other functional groups that can react with the sulfhydryl group of the cysteine to conjugate the peptide to the biocompatible polymer.

In general, the biocompatible polymer that will be conjugated with the peptide can be relatively low in molecular weight. For instance, the biocompatible polymer may have a number average molecular weight between about 1000 Da and about 10,000 Da. Use of a relatively low molecular weight polymer for the conjugation can increase the density of chain-ends, thus increasing the concentration of conjugated peptide in the electrospun fibers. This is not a requirement, however, and the biocompatible polymer that is conjugated with the peptide can have a higher molecular weight in other embodiments.

In one embodiment, a lactide-based polymer that has been terminated with an unsaturated double-bond such as an acrylamide group can be conjugated via a sulfhydryl functional group to the peptide that is terminated with a cysteine residue. For instance a polylactic acid formed via ring-opening polymerization of lactide monomer derived from lactic acid can be utilized. In other embodiments, commercially available polymers can be used. For example, poly (lactides) available from Polysciences, Inc., Natureworks, LLC, Cargill, Inc., Mitsui (Japan), Shimadzu (Japan), or Chronopol can be utilized.

The lactide-based polymer can be a homopolymer formed exclusively from the polymerization of lactide monomers. For example, the lactide monomer can be polymerized in the presence of a suitable polymerization catalyst, generally at elevated temperature and pressure conditions, as is generally known in the art. The catalyst can be any as is generally known, and can include alkyl lithium salts and the like, stannous octoate, aluminum isopropoxide, and certain rare earth metal compounds as described in U.S. Pat. No. 5,028, 667 and which is incorporated herein by reference. The particular amount of catalyst used can vary generally depending on the catalytic activity of the material, as well as the process temperature and the polymerization rate desired. Typical catalyst concentrations include molar ratios of lactide to catalyst of between about 10:1 and about 100,000:1, and in one embodiment from about 2,000:1 to about 10,000: 1.

The polymerization process is generally known in the art and thus is not described herein in detail. Briefly, in one embodiment the polymerization can be carried out at elevated temperature, for example, between about 95° C. and about 200° C. The temperature can generally be selected so as to obtain a reasonable polymerization rate for the particular catalyst used while keeping the temperature low enough to avoid polymer decomposition. In one embodiment, polymerization can take place at elevated pressure, as is generally known in the art. The polymerization typically takes between about 1 and about 72 hours, for example between about 1 and about 4 hours.

A polymer for conjugation with the peptide can be a homopolymer or a copolymer. For example, a copolymer that includes lactide monomer or oligomer in combination with one or more other polymeric materials can be utilized. In one embodiment, lactide can be co-polymerized with glycolide to form a biocompatible copolymer, as is known, and the lactide-based copolymer can be conjugated with the peptide.

The method of conjugating the biocompatible polymer with the peptide will vary depending upon the specific functional groups that are to be reacted in the conjugation reaction. When considering a sulfhydryl/acrylate reaction, for example, a Michael addition reaction protocol as is generally known can be utilized.

A solution including the biocompatible polymer conjugated to the peptide can be electrospun to form a fibrous sheet including nanofibers that incorporate the polymer. The solution can generally include a total polymer content of about 30% or less. In addition, the solution can include more than one polymer. For instance, the solution to be electrospun can include the polymer that is conjugated with the peptide in conjunction with one or more additional polymers.

The one or more additional polymers can be biocompatible resorbable polymers that can be the same or different as the biocompatible polymer that is conjugated to the peptide. By way of example, a low molecular weight polylactic acid that is conjugated to the acidic amino acid-containing peptide can be combined in the solution with a higher molecular weight polylactic acid homopolymer or copolymer and the solution can then be electrospun. In this embodiment, the polymer conjugated to the peptide can generally be included in the solution in an amount of about 10 wt. % or less, about 5 wt. % or less, or about 2 wt. % or less and the second polymer (or mixture of polymers) can be included in the solution from about 10 wt. % to about 20 wt. % of the solution.

In one embodiment, a second polymer in the electrospinning solution can be a high molecular weight biocompatible resorbable polymer. A high molecular weight polymer can facilitate fiber formation during electrospinning and the lower molecular weight peptide-conjugated polymer can diffuse during formation to the fiber surface to initiate nucleation of CaP crystals to the fiber surface during later processing.

The polymer(s) component of the electrospinning solution can generally have a glass transition temperature ($T_g$) of between about 50° C. and about 150° C., which is above physiological temperature and beneath thermal degradation temperature. This can be beneficial in those embodiments in which the electrospun sheet formed of the polymer fibers is to be heat treated (annealed) and fused into a desired shape, as discussed further herein.

The electrospinning process can be any process as is generally known in the art. In general, an electrostatic spinning process includes the application of an electrical field to the solution of the polymer, inducing a charge on the individual polymer molecules. The polymer solution can be held in a capillary tube by its surface tension at the air-surface interface. Upon application of an electric field, a charge and/or dipolar orientation will be induced at the air-surface interface that causes a force that opposes the surface tension. At critical field strength, the repulsive electrostatic forces will overcome forces due to the surface tension, and a jet of polymeric material will be ejected from the capillary tube. The jet is elongated and accelerated by the external electric field as it leaves the capillary tube. The trajectory of the jet can be controlled by applying an appropriately oscillated electrostatic field, allowing for directional control of the jet. As the jet travels in air, some of the solvent can evaporate, leaving behind charged polymer fibers that can be collected on a take-up reel. As the fibers are collected, the individual fibers may fuse, forming a fibrous sheet on the take-up reel. In addition, the polymer jet, after deposition on the collector, can also be further stretched by the tangential force produced by the rotation of the wheel and form aligned fibers on the edge of the wheel.

The critical field strength required to overcome the forces due to solution surface tension and form the jet will depend on many variables of the system. These variables include not only the particular polymers and solvents included in the solution, but also the polymer concentration and solution viscosity, as well as the temperature of the system. In general, characterization of the jet formed, and hence characterization of the fibers formed, depends primarily upon solution viscosity, net charge density carried by the electrospinning jet and surface tension of the solution. The ability to form the small diameter fibers depends upon the combination of all of the various parameters involved. For example, electrospinning of lower viscosity solutions will tend to form beaded fibers, rather than smooth fibers. In fact, many low viscosity, low molecular weight polymer solutions will break up into droplets or beads rather than form fibers when attempts are made to electrostatically spin the solution. Solutions having higher values of surface tension also tend to form beaded fibers or merely beads of polymer material, rather than smooth fibers.

The minimum polymer concentration of the solution to produce bead-free fibers is generally about 10 wt. %. Below the critical concentration, surface tension breaks the accelerating jet of fibers into droplets. Beneficially, the morphological structure of the electrospun nanofibers can have diameters similar to collagen fibers (e.g., about 50 to about 500 nanometers, with an average diameter of about 200 nanometers in one embodiment).

The fibrous sheet formed of the electrospun fibers can be removed from the take-up reel and used as a bone tissue biomimetic microsheet. There is no particular size limitations on the thickness of the sheets formed, though in general, a single sheet will not be so thick that would limit the diffusion of ions like calcium and phosphate ions within the fibrous sheet, as this will prevent optimum mineralization of the fibrous sheet. For instance, an individual electrospun fibrous sheet can be from about one micrometer to about 40 micrometer thick, or from about 5 micrometers to about 25 micrometers, for example about 5 micrometers in one embodiment, which can generate a fibrous sheet with a very high (e.g., greater than about 200%) mineral content, as discussed further herein.

While not wishing to be bound to any particular theory, it is believed that the electric field of the electrospinning process can affect the orientation of the polymers in the nanofibers, and can encourage the deposition of the acidic amino acid residues on the surface of the nanofibers. For instance, about 80% or more, such as about 82% or more or about 83% of the acidic amino acid residues can be on the surface of the nanofibers.

The nanofibers can include a high concentration of acidic amino acid residues on the surface, e.g., from about 1 nanomoles per square centimeter ($nmol/cm^2$) to about 10 nmol/cm² acidic amino acid residues can be on the surface of the nanofiber in the microsheet. In one embodiment from about 0.1 to about 0.2 acidic amino acid residues can be present per square nanometer of the nanofiber surface.

In order to encourage osteogenic differentiation of progenitor cells, the electrospun fibrous sheet can be further treated to mineralize the surface of the fibers. Specifically, the fibrous sheet can be incubated in a solution that includes the desired ionic mineral species, primarily calcium and phosphate, and the acidic amino acid residues can nucleate the desired minerals directly on the fibers. For example, the fibrous sheet can be incubated in a simulated body fluid (SBF) or a modified simulated body fluid (mSBF) that includes a mixture of calcium salts, phosphate salts, sodium chloride, potassium chloride, buffers, one or more organic acids, etc., and calcium phosphate crystals can nucleate from acidic amino acid residue directly on the surface of the nanofibers.

Organic acids as may be included in the solution can include biocompatible organic acids as are generally known in the art. For instance and without limitation, an incubation solution can include one or more of hydroxyl acetic acid, tartaric acid, citric acid, maleic acid, ascorbic acid, and so forth as well as mixtures of organic acids. The incubation solution can generally have a total organic acid concentration of about 20 mM or less, for instance from about 2 to about 10 mM in one embodiment. The mineral nucleation content can be increased with the addition of an organic acid to the incubation solution, but this effect can decrease as the organic acid content increases. For instance, in one embodiment the CaP content nucleated on a fibrous sheet can increase with organic acid content in the incubation solution up to a content of about 5 mM or about 10 mM, beyond which the mineral content nucleated on the fibrous sheet can decrease.

Depending upon the total incubation time, it may be beneficial to change the incubation solution periodically to replenish the calcium and phosphate ions as the crystals nucleate on the fibers. Beneficially, the nucleated crystals will be discreet on the surface of the nanofibers, which can leave uncoated fiber areas. This allows for further treatment of the materials, such as heat treatments, etc. that can be used to shrink, densify and/or fuse the fibers to other materials. As utilized herein, the term 'discreet' generally refers to crystals that are at least partially separated from one another. For instance, individual adjacent crystals may be fused to one another at a single location, but the individual crystals are still clearly separate crystals but for the point of fusion. Moreover, discreet crystals are not completely fused to adjacent crystals so as to form a uniform coating on a fiber—the discreet crystals nucleated on the fiber surface will allow for open areas between adjacent crystals.

The amount of nanocrystals formed on the fibrous sheet can depend upon the incubation time. For instance, incubation time can vary from about 2 hours to about 24 hours, and in that time, the amount of calcium phosphate nanocrystals nucleated on the fibrous sheets can vary from about 10 wt. % by weight of the fibers to about 300 wt. % by weight of the fibers. Of course, longer incubation times can be utilized (e.g., about 48 hours or longer) in order to form a fibrous sheet that includes a higher calcium phosphate deposition amount, but the maximum deposition time can generally be around 12 hours.

The CaP crystals that are nucleated on the surface of the nanofibers can have any shape. For instance, the nucleated crystals can be spherical, disc-like, cylindrical, amorphous, etc. While not wishing to be bound to any particular theory, it is believed that through selection and control of the specific materials of the incubation bath and the bath parameters (time, temperature, etc.), the crystal shapes can be controlled. FIG. 1 presents several different exemplary crystal shapes as may be grown including disk-like shapes (FIG. 1A), longer more spherical shapes (FIG. 1B), and more spherical shapes (FIG. 1C).

Following the calcium phosphate crystal nucleation, the fibrous sheet can exhibit excellent tensile modulus, for instance from about 100 megapascals (mPa) to about 1 gigapascal (GPa). Without wishing to be bound to any particular theory, it is believed that upon high nucleation of the calcium phosphate crystal, the individual crystals can overlap and fuse with one another at contact points between the discreet crystals and the fibers, forming a calcium phosphate/nanofiber network that can exhibit high mechanical characteristics such as high tensile modulus. In addition, the tensile modulus can be further increased upon heat treatment of the fibrous sheet. Heat treatment can generally be carried out at a temperature that is above the glass transition temperature of the fibers and below the melting temperature of the fibers. For instance, when considering a polylactic acid based fiber, heat treatment can be carried out at a temperature of between about 50° C. and about 150° C., for instance between about 60° C. and about 100° C. or about 80° C. in some embodiments.

Multi-layer materials can also be formed of the fibrous sheets. In order to form the multi-layer materials, the electrospinning/incubation process described above can be repeated in a layer-by-layer (LBL) formation process. For instance, following electrospinning and incubation of a first layer to nucleate calcium phosphate crystals on the first layer, the first layer can be adhered or attached to the take up reel of an electrospinning system and a second fibrous sheet can be formed on the first layer. This two-layer construct can then be incubated in the incubation solution so as to nucleate additional calcium phosphate crystals on the two-layer construct. Additional layers can likewise be formed and processed to form a multi-layered construct of the desired thickness. FIG. 2A presents a schematic image of a multi-layer sheet as may be formed by the layer-by-layer approach.

A multi-layered construct can dramatically increase nucleation and growth of apatite-like nanocrystals on the surface of nanofibers, leading to calcium phosphate content on the constructs in amounts that can be greater than about 160% or greater than about 200% by weight of the fibers. The tensile moduli of the multilayered constructs can likewise be quite high, for instance from about 500 mPa to about 5 GPa, in one embodiment. As with the single-layered sheets, the nucleated calcium phosphate crystals can continue to grow with incubation time and can fuse at contact points between the discreet crystals to form a network of fibers cross-linked with the discreet calcium phosphate crystals. It is speculated that the higher toughness of microsheets with the higher calcium phosphate content is related to the formation of this calcium phosphate cross-linked network of fibers.

Calcium phosphate content of the nanofibers can be further increased, for instance in order to reach that of cortical bone (about 300 wt. %) by reducing the thickness of individual fiber layers in the multilayer construct or by reducing porosity of the individual fiber sheets.

Beneficially, utilizing the disclosed methods, the extent of calcium phosphate nucleation and growth on the electrospun fibers, and in turn the fiber mechanical strength, can be controlled by incubation time in the ionic solution and/or by acidic amino acid residue density on the fiber surface, which can be varied by variation of the concentration in the fiber spinning solution.

The fibrous sheets can be used as formed for in vivo and in vivo applications. For instance, CaP nucleated fibrous sheets can be stacked and fused to one another to form a multi-layered laminated sheet for reconstruction in large bone defects such as calvarial defects.

One limitation of nanofiber fabrication by use of electrospinning is that it produces a relatively two dimensional fibrous sheets, even in the multi-layered construct embodiments. In addition, the pore sizes are relatively small, which does not allow cells to penetrate into the scaffold. To address such issues, the fibrous sheets can be perforated and used to fabricate three dimensional microtubes with different diameters.

Perforations can be formed in single fibrous sheets, multi-layered constructs, or three-dimensional constructs formed from single or multi-layered materials. Perforations can be formed by any suitable method, for instance utilization of a single needle or an array of needles that can perforate the sheets or three-dimensional shapes. Moreover, the perforations can be formed prior to incubation in a crystal deposition solution or following nucleation of the mineral crystals on the nanofibers, as desired. The perforations can generally be less than about 500 micrometers in diameter, for instance from about 10 to about 300 micrometers in diameter, or about 180 micrometers in diameter in one embodiment, which can avoid negatively impacting the strength characteristics of the sheets.

Following calcium phosphate nucleation, the sheets can be formed into three dimensional scaffold constructs. In one embodiment, for instance, small-diameter microtubuler constructs can be fabricated by wrapping a perforated, calcium-phosphate (CaP) deposited fibrous sheet around a mold. The mold can have the desired shape (e.g., cross sectional circular diameter, length, etc.) and the fibrous sheet can encircle the mold and have the desired axial length. Of course, the shape of the mold is not intended to be limited to cylindrical, and any desired mold shape can be utilized. Cylindrical molds can be utilized in one embodiment, however, as the shape can better mimic that of the osteons of the cortical bone. Moreover, the cylindrical constructs can be formed with a wide variety of diameters, e.g., from about 50 micrometers to about 1 millimeter. A mold can be wrapped once or multiple times by a fibrous sheet. For instance a single or multi-layered fibrous sheet can wrap a mold a single time or multiple times, depending upon the size of construct to be formed.

Following wrapping of the mold with the fibrous sheet, the sheet can be heat treated at a temperature that is above the glass transition temperature and below the melting temperature of the nanofibers. The heat treatment can shrink and densify the sheet as well as cause the fibrous sheet to maintain the shape of the mold and, in the case of multiple wrappings, fuse the multiple layers surrounding the mold to one another. FIG. 2B illustrates a perforated tubular-shaped construct as may be formed. Fusion of the fibrous sheets can also be carried out by subjection the materials to high pressure.

In one embodiment, a plurality of the microtubes can be bundled together coaxially (see, e.g., FIG. 2C) and fused via e.g., heat and/or pressure to form a three-dimensional construct. Any number of individual microtubes can be combined to form a larger construct, for instance from 2 to many thousands of microtubes can be combined. As stated previously, the three dimensional construct can also be perforated, either prior to molding and/or fusion or following, as desired. A three dimensional structure of microtubes with well-defined pores can be used to mimic the microstructure of osteons in cortical bone and induce osteogenesis of seeded cells such as seeded MSC and/or osteoblasts.

In one embodiment, the disclosed materials and constructs can be utilized for bone regeneration. For instance, the constructs can be seeded with cells (see, e.g., FIG. 2D) and utilized as a cellular scaffold for either in vivo or in vitro applications. Beneficially, the three dimensional bone tissue engineering scaffolds can be porous enough to support nutrients and oxygen transfer, mimic the micro and nanoscale features of the natural bone (e.g., the osteons), and can be composed of biodegradable and biocompatible material.

Overall, the materials and constructs that include the calcium phosphate nucleated nanofibers have the potential to provide a higher structural support to progenitor cells compared to materials previously utilized in bone tissue regeneration. For instance, following seeding with MSC, the disclosed three dimensional constructs can exhibit higher alkaline phosphatase activity, calcium phosphate deposition, collagen content and expression of principal osteogenic genes as compared to the relatively flat microsheets. In addition, the individual fabricated microtubes can be fused and larger scale tubular scaffolds for bone grafts application can be fabricated. The disclosed constructs provide a promising microenvironment that enhances osteogenesis compared to previously known materials.

The present invention may be better understood with reference to the Examples, set forth below.

Example 1

Cysteine-terminated EEGGC peptide (SEQ ID NO: 1) was synthesized manually on Rink Amide NovaGel™ resin (EMD Biosciences, San Diego, Calif.) in the solid phase and functionalized by the addition of a cysteine residue at the glycine end. Briefly, the Fmoc-protected amino acid (6 equiv), N,N'-di-isopropylcarbodiimide (6.6 equiv, DIC, Acros, Pittsburgh, Pa.) and hydroxybenzotriazole (12 equiv, HOBt, Acros) were added to 100 mg resin and swelled in N,N-Dimethylformamide (DMF, Acros). Next, 0.2 mL of 0.05 M N,N-dimethylaminopyridine (DMAP, Acros) was added to the mixture and the coupling reaction was allowed to proceed for 4-6 h at 30° C. with orbital shaking. The resin was tested for the presence of unreacted amines using the Kaiser reagent. After coupling the last amino acid, the EEGGC peptide (SEQ ID NO: 1) was cleaved from the resin and precipitated in cold ether. The peptide was purified by preparative HPLC and characterized by Finnigan 4500 Electro Spray Ionization (ESI) spectrometry (Thermo Electron, Waltham, Mass.). A similar procedure was used to synthesize EEGGKC peptide (SEQ ID NO: 2).

L-lactide (LA; >99.5% purity; Ortec, Easely, S.C.) monomer was dried under vacuum at 40° C. for at least 12 h prior to reaction. Low molecular weight poly(L-lactide) (LMW-PLA) was synthesized by ring-opening polymerization of LA monomer. Diethylene glycol (DEG, Fisher, Waltham, Mass.) and tin (II) 2-ethylhexanoate (TOC, Sigma-Aldrich) were used as the polymerization initiator and catalyst, respectively. The molar ratios of DEG:TOC and LA:DEG were 20:1 and 10:1, respectively. After the reaction, double precipitation in two non-solvents, diethyl ether and hexane, was used to fractionate and isolate the LMW-PLA. The synthesized polymer was characterized by gel permeation chromatography (GPC) and $^1$H-NMR. Next, the LMW-PLA chain was terminated with an acrylamide group by reaction with acryloyl chloride (Ac, Sigma-Aldrich). In a typical reaction, 20 g LMW-PLA was dissolved in 150 mL dichloromethane (DCM, Acros) under dry nitrogen atmosphere. After cooling to 5° C., 0.6 mL Ac and 1.55 mL triethylamine (TEA, Sigma-Aldrich), each dissolved in DCM, were added drop-wise to the reaction with stirring. The reaction continued for 6 h on ice followed by 12 h under ambient conditions. After the reaction, solvent was removed and residue was dissolved in anhydrous ethyl acetate to precipitate and remove the byproduct triethylamine hydrochloride. The Ac-PLA product was precipitated twice in hexane and cold ether, and dried in vacuum. The $\overline{M}_n$ and polydispersity index of the Ac-PLA were 5.3 kDa and 1.2, respectively.

EEGGC (SEQ ID NO: 1) or EEGGKC (SEQ ID NO: 2) peptide was conjugated to Ac-PLA by Michael addition reaction between the cysteine's sulfhydryl group on the peptide and the acrylate group on the polymer to produce the PLA-GLU or PLA-GLUK conjugate, respectively. Briefly, the peptide dissolved in sodium borate buffer (pH 8.5), was added to a solution of Ac-PLA in DMF (2:1 peptide:Ac-PLA molar ratio) and allowed to react for 12 h at 30° C. in an orbital shaker. The solution was then dialyzed (MW cutoff 3.5 kDa, Spectrum Laboratories, Rancho Dominguez, Calif.) against distilled deionized (DI) water and lyophilized to obtain the dry PLA-GLU conjugate. The chemical structure of the conjugate was characterized by $^1$H-NMR.

PLGA sample (Durect, Pelham, Ala.) was a 50/50 copolymer of D,L-lactide and glycolide monomers with intrinsic viscosity of 1.1 dL/g and weight average molecular weight of 105 kDa. A blend of 10 wt % high molecular weight PLGA and 1.5 wt % PLA-GLU was dissolved in 1, 1, 1, 3, 3, 3-hexafluoro-2-propanol (HFIP, VWR, West Chester, Pa.) solvent. A programmable KDS100 syringe pump (KD Scientific, Holliston, Mass.) was used to transfer and inject the polymer solution from a 1 mL syringe through a 21-gauge needle. The needle was connected to the positively charged Pt electrode of a high voltage power supply (ES40P-5W/DAM, Gamma High Voltage Research). A custom-built aluminum rotating wheel (20 cm diameter and 5 mm thickness), powered by a high-speed DC motor ((2M0578, Dayton Electric, Niles, Ill.) and connected to the ground electrode of the power source, was used to collect the aligned fibers (Xu et al., 2004; Yang et al., 2005). The rotating collector was placed 7.5 cm below the needle, with the edge of the wheel facing the needle. The electrospinning conditions of 1.0 mL/h injection rate, 20 kV electrical potential, and needle-to-collector distance of 7.5 cm were used (Ma et al., 2011). A rotation speed of 1200 rpm was used to produce aligned PLGA/PLA-GLU fibers, hereafter denoted by GLU-NF.

SEM was used to image the nanofibers. After coating with gold (Polaron sputter coater, Quorum Technologies, New Haven, UK) at 20 mA for 45 sec, the fiber mesh was attached to a SEM stub and imaged with a Field Emission Scanning Electron Microscope (FESEM, Carl Zeiss Microscopy, Hillsboro, Oreg.) at an accelerating voltage of 8 kV. SEM images were analyzed with ImageJ software (National Institutes of Health, Bethesda, Md.) to determine the average fiber size.

To determine surface coverage of GLU peptide on aligned nanofibers, the EEGGKC (SEQ ID NO: 2) peptide (GLUK) was conjugated to LMW-PLA. After electrospinning, the fibers were fluorescently labeled with fluorescein isothiocyanate (FITC, Sigma-Aldrich) in 5 mg/mL Dulbecco's phosphate-buffered saline (PBS, Cellgro, Herndon, Va.) for 4 h at ambient conditions. FITC, due to its size, reacts only with free lysine amine group of GLUK on the fiber surface. Therefore, assuming addition of lysine to EEGGC (SEQ ID NO: 1) peptide did not significantly change the peptide surface density, the FITC fluorescent intensity was related to GLU density on the fiber surface. FITC-labeled GLUK-conjugated nanofibers were imaged with an inverted fluorescent microscope (Nikon Eclipse Ti-$\epsilon$, Nikon, Melville, N.Y.). Next, the labeled nanofibers were dissolved in DMSO and fluorescent intensity was quantified with a Synergy HT plate reader (Bio-Tek, Winooski, Vt.) at emission and excitation wavelengths of 520 and 495 nm, respectively. Knowing mass and average size of the fibers, the intensities were converted into mass per unit surface area using a calibration curve generated by measuring the fluorescent intensity of solutions with known concentration of FITC in dimethylsulfoxide (DMSO, Sigma-Aldrich). PLGA nanofibers without EEGGKC (SEQ ID NO: 2) peptide dissolved in DMSO were used as negative control.

GLU-NF microsheets, approximately 25 μm thick, were incubated in a modified 10-fold concentrated simulated body fluid (m10SBF). Briefly, the stock solution of 10SBF was prepared by dissolving sodium chloride (NaCl), potassium chloride (KCl), calcium chloride monohydrate ($CaCl_2.H_2O$), magnesium chloride hexahydrate ($MgCl_2.6H_2O$), sodium bicarbonate ($NaHCO_3$), and monosodium phosphate ($NaH_2PO_4$), all purchased from Fisher, in DDI water. The final pH of 10SBF solution was 4.2. Next, 60 mM solution of $NaHCO_3$ was added to 10SBF stock solution to reach physiological pH of 7.4. Then, the suspension was centrifuged and filtered (220 nm pore size) prior to incubation. The modified-10SBF (m10SBF) solution was transparent after filtration, containing no CaP crystals when incubated with GLU-NF microsheets. During incubation, the containers were sealed with Parafilm to prevent a change in solution pH by $CO_2$ diffusion. The incubation solution was changed every 6 h to replenish calcium and phosphate components. At each time point, fiber sheets were washed with DI water and dried at ambient conditions.

In the layer-by-layer approach, the first GLU-NF microsheet, approximately 5 μm thick, was electrospun on a 12 mm circular glass coverslip (VWR, Bristol, Conn.). Next, the microsheet was incubated in m10SBF for the prescribed time, washed with DI, and dried. After drying, the second GLU-NF layer was electrospun directly on the first layer. The bilayer sheet was incubated in m10SBF for a prescribed time, washed with DI, and dried. This layer-by-layer process was repeated five times to produce a 26±2 μm thick mineralized multilayer GLU-NF circular sheet (12 mm diameter). The multilayer approach improved diffusion of calcium and phosphate ions inside the fiber sheet when incubated in m10SBF solution.

The mineralized microsheets were imaged with FESEM as described above. The calcium to phosphate ratio of the microsheets was measured by an energy-dispersive X-ray spectrometer (EDS) connected to FESEM at an accelerating voltage of 15 kV. The structure of CaP crystals on GLU-NF microsheets was determined by Wide-Angle X-Ray Diffraction (XRD) using a Philips diffractometer with CuKα radiation source at 30 kV (Model 405S5, Rigaku, Japan). The scanning range was from 10 to 50° with a step size of 0.05°. The water wettability of GLU-NF microsheets before and after mineralization was measured with a contact angle goniometer (Model DSA-20E, Kruss, Germany). A 10 μl drop of DI water was applied to the fiber surface, photographed immediately and contact angle (θ) was calculated from the height (h) and breadth (b) of the drop according to θ=arctan (2h/b).

The amount of CaP nucleation on the microsheets was measured using a QuantiChrom calcium assay (Bioassay Systems, Hayward, Calif.) according to manufacturer's instructions. Calcium content of the microsheets (0.3 mg) was dissolved in 0.4 mL of 1M HCl. Next, 5 μL aliquot of the suspension was added to 200 μL of the kit working solution. After 3 min incubation, absorbance was measured on a Synergy HT plate reader at a wavelength of 612 nm. Measured intensities were correlated to the equivalent amount of $Ca^{2+}$ using a calibration curve constructed with reference $CaCl_2$ solutions (zero to 200 μg/mL concentration). Total mineralized deposit of each sample was determined from the measured calcium contents at each time point (2, 4, 6, 12, and 24 hours) and the CaP ratios from EDS measurements, and divided by the fiber mass to find percent CaP. Tensile modulus of the samples was measured with a Rheometrics Dynamic Mechanical Analyzer (RSA III DMA, Piscataway, N.J.) with a strain rate of 0.033/s at ambient conditions. Samples were cut to dimensions of 20×5 mm and the maximum allowed strain was set at 160%. Thickness and width of the samples were measured with a micro-caliper (Mitutoyo, Aurora, Ill.) and modulus was calculated as the slope of the linear region of the stress-strain curve.

MSCs were isolated from the bone marrow of 6-8 weeks-old male Wistar rats. The marrow was flushed with 20 mL of cell isolation medium which consisted of Dulbecco's Modified Eagle's Medium (DMEM; 4.5 g/L glucose with L-glutamine and without sodium pyruvate, Cellgro, Herndon, Va.) and 10% Fetal bovine serum (FBS, Atlas Biologicals, Fort Collins, Colo.) supplemented with 100 units/mL penicillin (PN), 100 μg/mL streptomycin (SP), 20 μg/mL fungizone (FG), and 50 μg/mL gentamicin sulfate (GS), all purchased from Sigma-Aldrich. The cell suspension was cultured in basal medium (DMEM supplemented with 10% FBS, 100 units/mL PN, 100 μg/mL SP, 50 μg/mL GS, and 250 ng/mL FG). Cultures were replaced with fresh medium at 3 and 7 days to remove unattached cells. Cells were enzymatically lifted and used for cell culture experiments. For cell seeding, edges of the microsheets on 12 mm circular glass coverslip were coated with a medical-grade silicone sealant (Dow Corning, Mich.) to prevent separation of the mesh from coverslip. The construct was sterilized by ultraviolet (UV) radiation followed by immersion in 70% ethanol for 30 min and washing three times with sterile PBS. It has been demonstrated that UV radiation followed by immersion in ethanol is an effective procedure for sterilizing nanofibers. SEM images (not provided) show the morphology of GLU-NF nanofibers before and after ethanol incubation and washing steps during sterilization and the morphology GLU-NF/CaP50 nanofibers before and after sterilization. The images indicated that the sterilization procedure had no visible effect on the alignment or size of the fibers and attachment of CaP deposits to the fiber surface. After conditioning the fiber mesh in basal medium for 1 h, each sample was seeded with 60 μL MSC cell suspension ($1.7 \times 10^6$ cells/mL; $1 \times 10^5$ cells/cm$^2$) in basal medium. After incubation for 24 h for cell attachment, the medium was replaced with osteogenic medium (basal medium supplemented with 100 nM dexamethasone, 50 μg/mL ascorbic acid, 10 mM β-glycerophosphate) and cultured in a humidified 5% $CO_2$ incubator for up to 28 days. MSCs seeded on GLU-NF/LBL/CaP200 microsheets and incubated in basal medium without osteogenic factors (GLU-NF/LBL/CaP200-BM group) were used as the negative control group. To determine cell viability, MSCs seeded on the microsheets were stained with acetomethoxy derivative of calcein (cAM, Life Technologies, Grand Island, N.Y.) and ethidium homodimer (EthD, Life Technologies) to image live and dead cells, respectively. Stained samples were imaged with a Nikon Eclipse Ti-ε inverted fluorescent microscope. Cell viability was quantified by dividing the image into smaller squares and counting the number of live and dead cells manually.

At each time point (7, 14, 21, and 28 days), cell-seeded nanofibers were washed with serum-free DMEM for 8 h to remove serum proteins, followed by washing with PBS and lysed with 10 mM Tris supplemented with 0.2% triton in PBS. The lysed samples were used for measurement of DNA content, ALPase activity and calcium content. Double-stranded DNA content, ALPase activity and calcium content of the samples were measured with Quant-it PicoGreen assay (Invitrogen), QuantiChrom ALPase assay (Bioassay Systems) and QuantiChrom Calcium Assay (Bioassay Systems), respectively. To determine extent of mineralization of the samples, the measured intensities at time zero, used as baseline, were subtracted from those at days 7-28 to account for the deposited CaP prior to cell seeding. The measured ALPase activities and calcium contents were normalized to cell numbers by dividing to DNA contents at each time point.

For immunofluorescent staining, cell-seeded microsheets were washed twice in PBS and fixed with 4% paraformaldehyde (Sigma-Aldrich) at 4° C. for 12 h. Next, samples were permeabilized with 0.1% Triton X-100 and 100 mM glycine in PBS for 1 h and blocked with 1.5% BSA and 0.5 mM glycine in PBS for 2 h. Then, samples were incubated with primary antibodies in PBS containing 1% BSA for 24 h at 4° C. according to manufacturer's instructions. Primary antibodies from Santa Cruz Biotechnology (Santa Cruz, Calif.) included mouse anti-rat OP (1:100 dilution), rabbit anti-rat OC (1:100 dilution), and goat anti-rat Pecam-1 (1:50 dilution). After washing with PBS, samples were incubated with the secondary antibody (1:100 dilution) in blocking buffer for 2 h at ambient conditions. Secondary antibodies from Santa Cruz Biotechnology included donkey anti-mouse FITC-conjugated IgG, donkey anti-rabbit Texas-red conjugated IgG, and donkey anti-goat Texas-red conjugated IgG. It should be noted that each sample was stained with 4,6-diamidino-2-phenylindole (DAPI, Sigma-Aldrich) to image the cell nuclei and one of the antibodies for OC, OP, or Pecam-1. Secondary antibodies without the primaries were used as negative controls. For observation of cell morphology, cell-seeded GLU-NF microsheets were incubated with 0.16 μM Alexa Fluor® 594 phalloidin (Invitrogen) and 300 nM DAPI for 30 min at ambient conditions to stain the cell actin filaments and nuclei, respectively. The stained samples were imaged with a Nikon Eclipse Ti-ε inverted fluorescent microscope to observe cell morphology or expression pattern of the proteins with the same exposure time and light intensity.

At each time point (7, 14, 21, and 28 days), total cellular RNA was isolated using TRIzol (Invitrogen). 1 μg of the extracted purified RNA was subjected to cDNA conversion using Promega Reverse Transcription System (Madison, Wis.). The obtained cDNA was subjected to real time quantitative polymerase chain reaction (rt-qPCR) amplification with appropriate gene specific primers. The expression level of ribosomal protein S16 was used as the endogenous control. Primers for real-time PCR analysis were designed and selected using Primer3 web-based software. Real-time PCR (RT-qPCR) was performed to analyze differential expression of OP, ALPase, OC, Collagen type I (Col-1), Pecam-1 and Flk-1 genes with SYBR green Real-MasterMix (Eppendorf, Hamburg, Germany) using Bio-Rad CXF96 machine (Bio-Rad, Hercules, Calif.). Forward and reverse primers, shown in Table 1, were synthesized by Integrated DNA technologies (Coralville, Iowa).

TABLE 1

(SEQ ID NOS: 3-18, respectively, in order of appearance)

| Genes | Forward Primer | Reverse Primer |
|---|---|---|
| ALPase | 5'-CCT TGA AAA ATG CCC TGA AA-3' | 5'-CTT GGA GAG AGC CAC AAA GG-3' |
| Osteocalcin | 5'-AAA GCC CAG CGA CTC T-3' | 5'-CTA AAC GGT GGT GCC ATA GAT-3' |
| Osteopontin | 5'-GAC GGC CGA GGT GAT AGC TT-3' | 5'-CAT GGC TGG TCT TCC CGT TGC-3' |
| Collagen type-I | 5'-TGC CGA TGG CGC TAT C-3' | 5'-CAA GGG CCG GGG TGA CGC GGG-3' |
| PECAM-1 | 5'-CGA AAT CTA GGC CTC AGC AC-3' | 5'-CTT TTT GTC CAC GGT CAC CT-3' |
| Flk-1 | 5'-TAG CGG GAT GAA ATC TTT GG-3' | 5'-GGG GTG AGG ATG ACC GTG TA-3' |
| S16 | 5'-AGT CTT CGG ACG CAA GAA AA-3' | 5'-AGC CAC CAG AGC TTT TGA GA-3' |
| GAPDH | 5'-CGA CCT GGA AGT CCA ACT AC-3' | 5'-ATC TGC TGC ATC TGC TTG-3' |

Relative gene expression levels were quantified by the 2$^{-\Delta\Delta CT}$ method. Relative gene expressions were expressed as fold difference compared with that at time zero.

Data are expressed as means±standard deviation. All experiments were done in triplicate. Significant differences between groups were evaluated using a two-tailed Student's t-test. A value of p<0.05 was considered statistically significant.

Dissipative Particle Dynamics (DPD) method was used to simulate surface and bulk distribution of PLGA and PLA-GLU in the nanofibers by course-graining the macromers into different set of atoms or beads. Bead types included lactide, glycolide, acrylate, amino acid backbone chain, cysteine side group, and glutamic acid side group.

GLU peptide was covalently attached to Ac-PLA by the reaction between the acrylate group of Ac-PLA and cysteine residue of the peptide, as shown in FIG. 3A. $^1$H-NMR spectrum of Ac-PLA (inset) and PLA-GLU are shown in FIG. 3B. Chemical shifts with peak positions at 2.14, 2.32 and 4.57 were attributed to methylene and methine hydrogens of glutamate residues; that at 4.16 was attributed to methylene hydrogens of glycine residues; those at 5.19 and 8.03 were attributed to amine and amide hydrogens, respectively; and those at 3.11 and 3.77 were attributed to methylene and methine hydrogens of cysteine residue, respectively. Chemical shifts with peak positions at 1.78 and 5.35 ppm were attributed to methyl and methine hydrogens of lactide units, respectively; that at 3.64 ppm was attributed to methylene hydrogens of DEG in Ac-PLA. Chemical shifts with peak positions in the 6.04-6.48 ppm range were attributed to vinyl hydrogens of the acrylate end groups of Ac-PLA. Ratio of the peaks at 6.04-6.48 ppm (due to hydrogens of acrylate) to that at 5.35 ppm (due to hydrogens of lactide) was related to acrylate/LA molar ratio in Ac-PLA macromer. The number of peptides in the conjugate was determined using the acrylate/LA molar ratio before and after conjugation. Average number of peptides per conjugate was 1.3.

Concentration of PLA-GLU in the fibers ranged from zero to 2.5 mM. Average size of the aligned fibers was 200±60 nm. Image of PLGA/PLA-GLUK fibers, shown in FIG. 4A, showed intense fluorescent emission from FITC conjugation to the fiber surface. FITC-labeled fibers were dissolved in DMSO and fluorescent intensity was quantified and related to GLU peptide concentration, as shown in FIG. 4B. GLU density on the fiber surface increased linearly with PLA-GLU concentration up to 2 mM, followed by a slight, statistically not significant increase for higher concentrations. As PLA-GLU concentration was increased from 0.6 mM to 1.2, 2.0, 2.3 and 2.5 mM, GLU surface density increased from 5.4±1.2 to 12.3±0.9, 20.3±2.5, 20.7±2.7, and 21.1±2.3 nmol/cm$^2$, respectively. DPD simulation of PLGA/PLA-GLU nanofibers to predict GLU distribution on the fiber surface in a 30×20×20 $r_c$ simulation box without HFIP electrospinning solvent is shown in FIG. 4C. In the figure, beads other than GLU (dark) are shown lighter for clarity. The percentage of GLU groups on the fiber surface without and with 5% HFIP solvent was 82% and 83%, respectively, and the average number of GLU peptides on the surface was 0.16 GLU/nm$^2$.

Typical low magnification images of nanofibers (without GLU conjugation) and GLU-NF after incubation in m10SBF for 24 h are shown in FIG. 5A and FIG. 5B, respectively. FIG. 5C-FIG. 5F show higher magnification images of GLU-NF after incubation in m10SBF for 6, 24, 48 h, and LBL 24 h, respectively. CaP crystals nucleated from the fiber surface after 6 h incubation can be seen in FIG. 5C. As incubation time increased to 24 and 48 h, number of CaP crystals increased significantly, as shown in FIG. 5D and FIG. 5E, respectively. FIG. 5F shows uniform distribution of CaP crystals on fibers within as well as on the surface of microsheets. However, average size of the crystals did not change with incubation time and remained below 100 nm. The effect of GLU conjugation and CaP deposition on water wettability of the microsheets is shown in FIG. 6A-FIG. 6C. Water contact angel decreased to 85±3° (FIG. 6B) from 112±3° (FIG. 6A) after blending PLGA with PLA-GLU. The mineralized microsheets were completely wetted by water (zero contact angle, FIG. 6C). The measured contact angles were consistent with previously reported values for PCL modified with carboxylic acid groups. The amount of CaP crystals (based on fiber mass) deposited on NF (left, 1$^{st}$ bar), GLU-NF (middle, 2$^{nd}$ bar), and GLU-NF/LBL (right, 3$^{rd}$ bar) microsheets with incubation time is shown in FIG. 6D. As incubation time increased from 2 to 4, 6, 12, and 24 h, amount of CaP deposited on NF microsheets changed from 2.8±2.2% to 8.7±0.9, 8.6±2.5, 11.6±1.0, and 12.1±2.5%, respectively, while the amount deposited on GLU-NF microsheets increased from 13.3±0.7% to 28.0±3.8, 29.4±4.5, 37.0±5.1, and 50.0±5.6%. Amount of CaP deposited on NF microsheets did not increase significantly with incubation time while CaP deposition on GLU-NF sheets increased significantly (indicated by one star). Interestingly, amount of CaP deposited with the LBL approach (24 h incubation in each layer) increased to 203±5% compared to 50.0±5.6% for a single 25 µm layer. These results indicated that the GLU peptide provides sites for nucleation of CaP crystals and CaP deposition is limited by the diffusion of calcium/phosphate ions to the interior part of GLU-NF microsheets.

Tensile modulus and toughness of GLU-NF microsheets are given in FIG. 6E and FIG. 6F, respectively. Tensile modulus increased significantly with extent of CaP deposition on the fibers, especially in the LBL approach. Tensile modulus increased from 260±10 MPa for GLU-NF to 330±17, 540±15, and 880±40 MPa for GLU-NF with 30% (6 h incubation), 50% (24 h incubation), and 200% (LBL) CaP deposition. There was a sharp increase in toughness when CaP deposition was increased to 50% and 200%, indicating overlap/fusion of crystals on the fibers and formation of a CaP-NF network. XRD spectra of NF (middle) and GLU-NF (bottom) microsheets after 24 h incubation in m10SBF are compared in FIG. 6G with that of synthetic apatite nanocrystals (top, Berkeley Biomaterials, Berkeley, Calif.). CaP crystals deposited on GLU-NF microsheets showed the characteristic apatite peaks centered at 31.8°, 25.8° ' and 47° (Kim et al., 2005) while NF sheets without GLU did not show those peaks. Ca/P ratio of the crystals was 1.58±0.1, based on the EDS spectrum of GLU-NF microsheets after 24 h incubation in m10SBF as shown in FIG. 6H, which was in the reported range of 1.4-1.7 for CaP crystals in the natural bone and close to 1.67 for synthetic apatite crystals (Chen and Chang 2011). Similar results were obtained for GLU-NF microsheets incubated in m10SBF for different times.

MSCs were seeded on GLU-NF, GLU-NF with 30% (GLU-NF/CaP30), 50% (GLU-NF/CaP50), and 200% (GLU-NF/LBL/CaP200) CaP content, and cultured in osteogenic medium for 28 days. MSCs seeded on GLU-NF/LBL/CaP200 with highest CaP content of 200% and incubated in basal medium was used as the negative control group (GLU-NG/LBL/CaP200-BM) for biochemical, mRNA and immunocytochemical analysis. To observe the morphology of individual cells, MSCs were seeded on the microsheets at low density of 1500 cells/cm$^2$ and incubated in osteogenic medium. Fluorescent images (FIG. 7A-FIG. 7D) of cell nuclei and cytoskeletal actin filaments in FIG. 7 shows morphology of the MSCs seeded on GLU-NF (FIG. 7A), GLU-NF/CaP30 (FIG. 7B), GLU-NF/CaP50 (FIG. 7C), and GLU-NF/LBL/CaP200 (FIG. 7D) microsheets after two days of incubation. The images indicate that the seeded cells completely aligned with fiber direction even after CaP deposition. Inset images in FIG. 7 show the corresponding morphology of MSCs with initial seeding density of 1×10$^5$ cells/cm$^2$ after 7 days of incubation in osteogenic medium. The seeded MSCs displayed an elongated morphology in the direction of the fibers for all CaP contents at higher density and longer incubation time. Images of live and dead MSCs two days after cell seeding at high density on the microsheets (not shown) showed >90% cell viability two days after cell seeding (1×10$^5$ cells/cm$^2$) and incubation in osteogenic medium.

DNA content of MSCs cultured on GLU-NF/CaP microsheets is shown in FIG. 8A. DNA content of GLU-NF/LBL/CaP200-BM (1) incubated in basal medium, in the absence of osteogenic differentiation factors, increased slightly with incubation time while those incubated in osteogenic medium decreased significantly with time. The cell density for CaP deposited microsheets on day 7 was significantly higher than that of GLU-NF, as indicated by a star in FIG. 8A. Cell number results suggested that the CaP deposited microsheets did not have a toxic effect on the seeded cells and the decrease in DNA content of MSC-seeded microsheets incubated in osteogenic medium was related to cell differentiation or the initial seeding density.

ALPase activity of MSCs seeded on GLU-NF/CaP microsheets is shown in FIG. 8B. ALPase activity of MSCs seeded on GLU-NF/LBL/CaP200-BM microsheets incubated in basal medium did not increase with time (1). ALPase activity of all other groups, incubated in osteogenic medium, peaked after 14 days and returned to baseline level at day 28. ALPase activity increased significantly with amount of CaP deposition on the fibers. For example, peak ALPase activity of GLU-NF/CaP30, GLU-NF/CaP50, and GLU-NF/LBL/CaP200 increased from 2400±200 to 3200±600 and 5100±400 IU/mg DNA, respectively, while that of GLU-NF was 1600±100 IU/mg. Calcium content of MSCs seeded on CaP-deposited microsheets is shown in FIG. 8C. All calcium measurements were subtracted from the amount at day 4 to remove the calcium due to CaP deposition prior to cell seeding. For all groups, extent of mineralization of the MSCs increased gradually from day 14 to 28 with GLU-NF/LBL/CaP200 having the highest mineralization after 28 days of incubation in osteogenic medium. Mineral content of the MSCs seeded on GLU-NF/LBL/CaP200-BM incubated in basal medium increased slightly with time, which could be related to the osteogenic effect of deposited CaP prior to cell seeding. For example, calcium content of MSC-seeded GLU-NF/LBL/CaP200 microsheets after 28 days was 960±110 mg/mg DNA, while those of GLU-NF/LBL/CaP200-BM, GLU-NF, GLU-NF/CaP30, and GLU-NF/CaP50 were 130±20, 460±40, 580±40, and 760±80 mg/mg DNA, respectively.

Expression of osteogenic markers OP, ALPase, OC, Col-1, and vasculogenic markers Pecam-1 and Flk-1 with incubation time for MSC-seeded GLU-NF/CaP microsheets is shown in FIG. 9A through FIG. 9F, respectively. For GLU-NF/LBL/CaP200-BM control group incubated in basal medium, expression of OP, ALPase, OC, Pecam-1, and Flk-1 did not change significantly with time, while there was a significant increase in Col-1 expression. However, the increase was significantly less than those microsheets incubated in osteogenic medium (FIG. 9D). ALPase mRNA expressions for all groups followed their corresponding ALPase activity shown in FIG. 9B, peaking at day 14 and returning to baseline level at day 28. mRNA expression of OP, OC, and Col-1 increased gradually with incubation time. Expression of osteogenic marker OP was highest for GLU-NF/LBL/CaP200, as shown in FIG. 9A. For example, OP expression of GLU-NF/LBL/CaP200 at day 28 was 68±4 while those of GLU-NF, GLU-NF/CaP30, and GLU-NF/CaP50 was 16±2 and 25±3, 48±3, respectively. Expression of osteogenic markers OC and Col-1 followed a similar trend with GLU-NF/LBL/CaP200 having the highest expression (420±30). For example, OC expression of GLU-NF, GLU-NF/CaP30, GLU-NF/CaP50, and GLU-NF/LBL/CaP200 at day 28 was 180±10, 250±30, 300±20, and 420±30, respectively, while that of Col-1 was 6±1, 11±2, 14±1, and 16±1. Expression of Pecam-1 and Flk-1 of the MSCs did not change significantly with incubation time and CaP deposition, which indicated that CaP deposition on the fibers mainly affected osteogenic expression. Pecam-1 and Flk-1 expression for GLU-NF/LBL/CaP200 was slightly higher than the other groups at day 28 (FIG. 9E and FIG. 9F).

FIG. 10 shows immunostained images of MSCs seeded on GLU-NF/CaP microsheets. Columns a through c in FIG. 10 are for OC, OP, and Pecam-1, respectively, and rows 1-5 are for GLU-NF/LBL/CaP200-BM incubated in basal medium as negative control, GLU-NF, GLU-NF/CaP30, GLU-NF/CaP50 and GLU-NF/LBL/CaP200 after 28 days of incubation in osteogenic medium. GLU-NF/LBL/CaP200-BM did not stain for OC, OP, or Pecam-1 markers. GLU-NF group showed weak staining for all three markers while the CaP deposited GLU-NF groups showed moderate to strong staining for osteogenic markers OC and OP. There was a slight increase in Pecam-1 staining for GLU-NF/LBL/CaP200 group, consistent with the slight increase in mRNA expression in FIG. 9E. Overall, GLU-NF/LBL/CaP200 group showed highest staining for OC, OP, and Pecam-1. Taken together, results in FIG. 8-FIG. 10 demonstrate that the extent of osteogenic differentiation of MSCs seeded on GLU-NF microsheets depended strongly on the amount of deposited CaP on the fibers prior to cell seeding.

The simulated percentage of GLU groups on the fiber surface was >80%. Although diameter of the simulated fibers was significantly less than the actual fiber diameter, simulation results indicated that a major fraction of GLU peptides localized to the fiber surface. It should be noted that the simulations were performed in the absence of electric field, thus the actual GLU percentages on the fiber surface may be higher than the predicted values. The simulation results taken together with contact angle measurements in FIG. 6A and fluorescence measurements of FITC labeled PLA-GLUK fibers in FIG. 4B provide evidence for localization of a significant fraction of PLA-GLU to the fiber surface when blended with PLGA, to serve as nucleating sites for CaP deposition.

Conjugation of GLU sequence reduced water contact angle on the fiber surface, as shown in FIG. 6A-FIG. 6C, with zero contact angle after CaP deposition on the fibers. The finite water contact angle of <90° on GLU-NF fibers allowed nucleation and growth of CaP crystals on layers near the fiber surface but it limited penetration of water, calcium, and phosphate ions inside the microsheets. Consequently, when incubation time of GLU-NF microsheets in m10SBF was increased from 24 to 48 h, there was little change in CaP content and tensile modulus (data not shown). When the LBL approach was used to produce CaP-deposited microsheets, there was a dramatic increase in CaP content from 50±6 to 200±5%, as shown in FIG. 6D, indicating that CaP nucleation and growth on GLU-NF fibers was controlled by diffusion of calcium/phosphate ions from the medium to inside the microsheets. It should be noted that the CaP content of LBL microsheets was between those of cancellous (160%) and cortical (310%) bone, demonstrating that CaP contents as high as that of cortical bone can be achieved by reducing layer thickness. The LBL approach has been used to increase filler loading and stiffness of composites or fabricate highly ductile oppositely charged multilayered films.

The tensile modulus and toughness of the microsheets dramatically increased with higher CaP contents of 50 and 200%, as shown in FIG. 6E and FIG. 6F, respectively. These results indicate that fiber size, CaP crystal size, and nucleation and growth of CaP crystals on the fiber surface contribute to the higher modulus and toughness of the microsheets.

DNA content of the MSCs seeded on GLU-NF/LBL/CaP200 microsheets incubated in osteogenic medium decreased significantly with time, as shown in FIG. 8A. However, the slight increase in DNA content of MSCs on GLU-NF/LBL/CaP200 microsheets incubated in basal medium (1 in FIG. 8A) indicated that the microsheets did not have toxic effect on the seeded cells. It is speculated that the decrease in cell number with incubation time in osteogenic medium was related to cell differentiation as well as the initial cell seeding density. At relatively low initial density of 3000 cells/cm$^2$ (data not shown), DNA content of the MSCs on the microsheets increased significantly for all time points in osteogenic medium and DNA content was relatively independent of the extent of CaP deposition prior to cell seeding. As the initial cell density was increased to $2.5 \times 10^4$ cells/cm$^2$, DNA content increased in the first 7 days and then remained relatively constant (or increased slightly) for times between 7 and 28 days as the cells differentiated in osteogenic medium. With further increase in initial cell density to $1 \times 10^5$ cells/cm$^2$ (FIG. 8A), DNA content of the MSCs on the microsheets decreased significantly for all time points with incubation in osteogenic medium, but remained relatively unchanged in basal medium (FIG. 8A, 1). Images of live and dead MSCs two days after cell seeding on the microsheets showed >90% cell viability two days after seeding in osteogenic medium, implying that the microsheets did not have a significant toxic effect on the seeded cells. Taken together, these results demonstrate that the change in DNA content of the MSCs seeded on the microsheets with incubation time depended on the initial cell seeding density and culture medium (osteogenic versus basal medium). It appears that cell-cell contact plays a significant role in osteogenic differentiation of MSCs and other stem cells. Based on previous studies, a relatively high seeding density of $1 \times 10^5$ cells/cm$^2$ was used to investigate osteogenic differentiation of rat MSCs on GLU-NF microsheets.

Biochemical, mRNA, and immunocytochemical results show that the extent of osteogenic differentiation and maturation of MSCs seeded on the microsheets increased with CaP deposition. This increase can be explained by the higher modulus as well as higher CaP content of GLU-NF microsheets prior to cell seeding. These results show that osteogenic differentiation of MSCs depends directly on the extent of CaP deposition on the nanofibers prior to cell seeding. The extent of osteogenic differentiation of MSCs may also depend on the connectivity of crystals with increasing CaP deposition.

Example 2

NF microsheets were fabricated by electrospinning a solution of 10 wt % PLGA concentration at al 0.0 µL/h injection rate, 20 kV electric potential, 7.5 cm needle-to-wheel distance, 20 cm wheel diameter, and 1200 rpm rotation speed of the wheel as described in Example 1, above. The microsheets were mineralized as described above in Example 1. Specifically the glutamic acid conjugated NF nucleated with CaP crystals on fiber sheets with a 50 wt % CaP to fiber ratio (GLU-NF/CaP50)

SEM images are provided of GLU-NF (FIG. 11A), GLU-NF/CaP30 (FIG. 11B), GLU-NF/CaP50 (FIG. 11C), and LBL/CaP200 microsheets (FIG. 11D). CaP crystals nucleated from the fiber surface after 6 h incubation can be seen in the images. As incubation time increased to 24 h, the amount of CaP crystals increased significantly, as shown in FIG. 11C. FIG. 11D shows CaP nucleated nanofibers by layer-by-layer application, as it is seen in the image the content of CaP crystals with the average size of 100 nm increased significantly with layer-by-layer method.

The microsheets were heat treated by annealing at 80 C.° for 10 min. An image of GLU-NF microsheets before and after heat treatment is shown in FIG. 12A and FIG. 12B. The average size of the microsheets before and after heat treatment was 8.7×10.7×0.05 mm, 9.7×13.2×0.04 mm, respectively. The heat treatment resulted in the significant shrinkage of the nanofiber microsheets.

The effects of heat treatment on GLU-NF, GLU-NF/CaP30, GLU-NF/CaP50, and LBL/CaP200 microsheets based on CaP to NF weight ratio porosity and density were determined. The porosity and density of the CaP nucleated NF microsheets before and after heat treatment were calculated using Eq. (1) and Eq. (2), below.

$$\text{Appeareant Density (mg/mm}^3\text{)} = \frac{\text{microsheet mass (mg)}}{\text{thickness} \times \text{surface area (mm}^2\text{)}} \quad (1)$$

$$\text{Porosity (\%)} = \left(1 - \frac{\text{density of microsheets (mg/mm}^2\text{)}}{\text{density of PLGA (mg/mm}^2\text{)}}\right) \times 100\% \quad (2)$$

The results indicated that the porosity of the CaP nucleated microsheets after heating decreased significantly for all the test groups (FIG. 12C). In addition, the apparent density of different CaP-containing GLU-NF microsheets was increased significantly for each test group after heat treatment (FIG. 12D). The tensile modulus of microsheets before and after heat treatment is shown in FIG. 12E. The heat treatment significantly increased the tensile modulus of the CaP nucleated GLU-NF microsheets. For example, the tensile modulus of GLU-NF/CaP50 microsheets increased from 539±3 MPa to 770±65 MPa. It was demonstrated that there was a significant increase in tensile modulus on GLU-NF/CaP50 microsheets after heat treatment (one star). These results indicated that the stiffness of GLU-NF/CaP50 microsheets was increased by heat-shrinking the microsheets.

The fiber sheets were used to fabricate osteon-mimetic microtubes.

Specifically, uniform micropores were created in each microsheet by use of a 29 GTV needle (PrecisionGlide, 0.34 mm O.D., Becton-Dickinson, Franklin, N.J.). Following, the CaP nucleated electrospun microsheets (5 cm length×1 cm width) were wrapped around a 21 GTW needle (Precision-Glide, 0.81 mm O.D., Becton-Dickinson, Franklin, N.J.) and placed in pre-heated 80 C.° oven for 10 min to anneal the structure of the microsheet and keep its microtubalar structure by shape memory effect.

An SEM image of micropores in a microsheet is shown in FIG. 13A and SEM images of microtubes following heat treatment are shown in FIG. 13B-FIG. 13F. The average size of the micropores was 180 μm.

Multiple microtubes were then bundled together by annealing at 80 C.° for 10 min. FIG. 13C shows a bundle of microtubes average size of 450 μm. Microtubes were fabricated with different inner diameters by wrapping the perforated microsheets around different size needles. FIG. 13 includes SEM images of different inner diameter microtubes including 150 μm (FIG. 13D), 350 μm (FIG. 13E), and 800 μm (FIG. 13F).

The microsheets and tubes were seed with MSCs as described in Example 1. Immunohistochemistry images of MSCs for CD73, CD90, VE-cadherin, and CD-31 (PECAM-1) are shown in FIG. 14. The results indicated that MSCs had strong CD73 and CD90 expression, whereas there was no VE-cadherin and CD-31 expression.

In order to observe the morphology of individual cells, MSCs were seeded on the microsheets at low density of 1500 cells/cm² and incubated in osteogenic medium. Fluorescent images of cell nuclei and cytoskeletal actin filaments in FIG. 14B(1), FIG. 14B(2), FIG. 14B(3) and FIG. 14B(4) show morphology of the MSCs seeded on GLU-NF ($1^{st}$ row), GLU-NF/CaP30 ($2^{nd}$ row), GLU-NF/CaP50 ($3^{rd}$ row) and LBL/CaP200 microsheets ($4^{th}$ row) after two days of incubation. The images indicate that the seeded cells completely aligned with fiber direction irrespective with CaP nucleation. Inset images show the SEM images of GLU-NF ($1^{st}$ row), GLU-NF/CaP30 ($2^{nd}$ row), GLU-NF/CaP50 ($3^{rd}$ row), and LBL/CaP200 microsheets ($3^{rd}$ row).

MSCs were seeded on GLU-NF/CaP50 based microsheets (MS, control), 0.35 mm (MT, 0.35 mm), and 0.8 mm (MT, 0.8 mm) diameter microtubes and cultured in osteogenic media for 28 days. DNA content, ALPase activity, calcium content, and total collagen content of the MSCs were analyzed as a function of incubation time. FIG. 15A shows the DNA content of the MSCs on the microsheets (MS, control, 3), 0.35 mm (2), and 0.8 mm (1) diameter microtubes as a function of incubation time. The time points for osteogenic differentiation of MSCs were 7, 14, and 28 days. The results indicated that there was no significant difference in the DNA content between MSCs seeded inside 0.8 mm microtubes and onto microsheets (control) at each time point. Since the cell seeding density was kept constant for all experimental groups ($1 \times 10^5$ cells/cm²), the DNA content in 0.35 mm microtubes was significantly lower than 0.8 mm microtubes and microsheets. In addition, the CaP deposited microsheets and formed microtubes did not have a toxic effect on the seeded cells.

ALPase activity of the MSCs on microsheets (control, 3), 0.8 mm (1), and 0.35 mm (2) diameter microtubes as a function of incubation time is shown in FIG. 15B. In the experimental groups, ALPase activity peaked after 14 days. It then started to decrease gradually for both microsheets and microtubes cultures. The results indicated that there was a significant difference on ALPase activity of MSCs seeded inside 0.35 mm, and 0.8 mm microtubes compared to microsheets (indicated by one star) on day 14. However, there was no significant difference between microsheets and microtubes on day 28. For example, the peak value of ALPase activity of MSCs on microsheets, 0.35 mm, and 0.8 mm microtubes was 2583±131, 4370±654, and 5275±685 IU/mgDNA at day 14, respectively. ALPase activity of all other groups, incubated in osteogenic medium, peaked after 14 days and returned to baseline level at day 28. In addition, there was no significant difference on the ALPase activity of 0.35 mm and 0.8 mm microtube groups. These results indicated that the inner diameter of the microtubes did not affect the ALPase activity of MSCs.

Calcium content of the MSCs on microsheets and in microtubes (0.35 mm and 0.8 mm) as a function of incubation time is shown in FIG. 15C. Microtubes (0.35 mm and 0.8 mm) had significantly higher amount of calcium content compared to microsheets on days 14 and 28 days (indicated by one star). For example, the calcium content on microsheets was 453±59 mg Ca/mg DNA on day 28, while that of the 0.35 mm microtubes was 453±59, and that of the 0.8 mm microtubes was 635±41 mg Ca/mg DNA. However, there was no significant difference in the 0.35 mm and 0.8 mm microtube groups for calcium content. All calcium measurements were subtracted from the amount at day 0 to remove the calcium due to CaP deposition prior to cell seeding. For all groups, extent of mineralization of the MSCs increased gradually from day 7 to 28 in osteogenic medium.

The total collagen production in microtubes (0.35 and 0.8 mm) and on microsheets (control) is shown in FIG. 15D. It was demonstrated that there was a significant increase in the collagen secretion in microtubes (0.35 and 0.8 mm) when compared with the control at 7, 14 and 28 days (indicated by one star). The secretion of newly formed collagen is important to enhance the stability of the mineralized microtubes and microsheets during the culture. For example, the total collagen production of MSCs on microsheets and in microtubes (0.35 and 0.8 mm) was 472±75, 821±95, and 983±127 μg collagen/μg DNA after 28 days, respectively. However, there was no significant difference in collagen secretion between the 0.35 mm and 0.8 mm microtubes. Moreover, the total collagen content gradually increased in both microtubes and microsheets culture with the increase of incubation time.

As there was no significant difference detected in the biochemical assays, the expression levels of the osteogenic markers, ALPase, OC, and Col-1 as a function of incubation time were only measured for 0.8 mm microtubes and microsheets (control). Results are shown in FIG. 15E, FIG. 15F and FIG. 15G, respectively. One star indicates a significant difference between microsheets (control) and microtubes (0.8 mm) at the same time point. At day 14, 21, and 28, MSCs seeded in microtubes had a significantly higher OP expression compared to MSCs seeded on microsheets (one star). After 14 days, MSCs seeded in microtubes had a significantly higher ALPase expression compared to MSCs on microsheets (control). MSCs in microtubes had significantly higher Col-1 and OC expressions compared to MSCs on microsheets on day 28. However, there was no significant difference at earlier time points. Overall, OC and Col-1 expression gradually increased with the incubation time, while ALPase increased within the first 14 days and then returned to the base line on day 28, consistent with the ALPase activities shown in FIG. 15B. MSC differentiation into an osteogenic lineage occurs in a two-stage maturation process, where ALPase increases and peaks in the early stage of osteogenic differentiation and mineralization, and then decreases while calcium content starts to increase. For both experimental groups, the DNA content after 7 days started to decrease gradually. It has been previously demonstrated that differentiation of MSCs in osteogenic media significantly reduces the proliferation of MSCs.

Although the initial cell seeding density was equal for the experimental groups, the ALPase activity of the MSCs grown in the microtubes was significantly higher than microsheets culture. Calcium secretion of MSCs for microsheets and microtubes increased gradually with time. This result is consistent with previous results that showed the calcium content of MSCs on aligned and random PLAA NF significantly increased with time. High ALPase expression is a marker of maturation phase of MSCs, while high expression of OC and OP represents mineralization phase of osteogenic differentiation of MSCs. In addition, it is known that ALPase expression decreases during the mineralization phase of MSCs. The increase in expression levels of osteogenic markers OC and OP with incubation time is consistent with previously reported results for MSCs.

While the present subject matter has been described in detail with respect to specific exemplary embodiments and methods thereof, it will be appreciated that those skilled in the art, upon attaining an understanding of the foregoing may readily produce alterations to, variations of, and equivalents to such embodiments. Accordingly, the scope of the present disclosure is by way of example rather than by way of limitation, and the subject disclosure does not preclude inclusion of such modifications, variations and/or additions to the present subject matter as would be readily apparent to one of ordinary skill in the art.

What is claimed is:

1. A method for forming a bone tissue biomimetic material comprising:
   electrospinning a first solution to form a first fibrous sheet including nanofibers, the first solution including a biocompatible polymer conjugated to a peptide, the peptide comprising multiple acidic amino acid residues; and
   incubating the first fibrous sheet in a simulated body fluid that includes calcium ions, phosphate ions, and an organic acid, calcium phosphate crystals nucleating on the nanofibers of the first fibrous sheet during the incubation.

2. The method of claim 1, wherein the peptide is derived from a bone extracellular matrix protein.

3. The method of claim 1, wherein the acidic amino acid residues comprise glutamic acid or aspartic acid.

4. The method of claim 1, the method further comprising:
   electrospinning a third solution to form a second fibrous sheet including nanofibers;
   locating the second fibrous sheet on a surface of the first fibrous sheet following the nucleation of the calcium phosphate crystals and thus forming a multi-layer fibrous sheet; and
   incubating the multi-layer fibrous sheet in a fourth solution comprising calcium ions, phosphate ions, and an organic acid, calcium phosphate crystals nucleating on the multi-layer fibrous sheet during the incubation.

5. The method of claim 4, further comprising repeating the electrospinning and incubation steps to add additional layers to the multi-layer fibrous sheet.

6. The method of claim 1, the first solution further including a second biocompatible polymer.

7. The method of claim 1, the peptide including from 2 to 10 acidic amino acid residues.

8. The method of claim 1, wherein the biocompatible polymer is conjugated to the peptide via a cysteine residue of the peptide.

9. A method for forming a bone tissue biomimetic structure comprising:
   wrapping the first fibrous sheet of claim 1 around a mold following the step of incubating the first fibrous sheet in the simulated body fluid, the mold having a circular cross section and an axial length, the first fibrous sheet being wrapped around the mold such that it encircles the mold and extends along at least a portion of the axial length of the mold with a tubular shape;
   heat treating the first fibrous sheet; and
   removing the mold from the first fibrous sheet, the first fibrous sheet retaining the tubular shape following the removal of the mold.

10. The method of claim 9, further comprising perforating the first fibrous sheet either prior to or following wrapping the first fibrous sheet around the mold.

11. The method of claim 9, further comprising wrapping the first fibrous sheet around the mold multiple times to form a multi-layered tubular shape, the layers of the multi-layered tubular shape fusing to one another upon the heat treatment.

12. The method of claim 9, further comprising fusing a plurality of the tubular-shaped first fibrous sheets by application of heat or pressure to the plurality to form a multi-tubular construct.

\* \* \* \* \*

SEQUENCE LISTING

```
<160> NUMBER OF SEQ ID NOS: 18

<210> SEQ ID NO 1
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Glu Glu Gly Gly Cys
1               5

<210> SEQ ID NO 2
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Glu Glu Gly Gly Lys Cys
1               5

<210> SEQ ID NO 3
<211> LENGTH: 20
<212> TYPE: DNA
<213> ORGANISM: Artificial Sequence
<220> FEATURE:
<223> OTHER INFORMATION: Description of Artificial Sequence: Synthetic
```

```
          primer

<400> SEQUENCE: 3
ccttgaaaaa tgccctgaaa                                                  20

<210> SEQ ID NO 4
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
cttggagaga gccacaaagg                                                  20

<210> SEQ ID NO 5
<211> LENGTH: 16
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
aaagcccagc gactct                                                      16

<210> SEQ ID NO 6
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
ctaaacggtg gtgccataga t                                                21

<210> SEQ ID NO 7
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
gacggccgag gtgatagctt                                                  20

<210> SEQ ID NO 8
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
catggctggt cttcccgttg c                                                21

<210> SEQ ID NO 9
<211> LENGTH: 16
<212> TYPE: DNA
<213> ORGANISM: Artificial Sequence
<220> FEATURE:
<223> OTHER INFORMATION: Description of Artificial Sequence: Synthetic
      primer
```

```
<400> SEQUENCE: 9
tgccgatggc gctatc                                                       16

<210> SEQ ID NO 10
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
caagggccgg ggtgacgcgg g                                                 21

<210> SEQ ID NO 11
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
cgaaatctag gcctcagcac                                                   20

<210> SEQ ID NO 12
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12 cttttttgtcc acggtcacct                                                  20

<210> SEQ ID NO 13
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
tagcgggatg aaatctttgg                                                   20

<210> SEQ ID NO 14
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
ggggtgagga tgaccgtgta                                                   20

<210> SEQ ID NO 15
<211> LENGTH: 20
<212> TYPE: DNA
<213> ORGANISM: Artificial Sequence
<220> FEATURE:
<223> OTHER INFORMATION: Description of Artificial Sequence: Synthetic
      primer
```

```
<400> SEQUENCE: 15
agtcttcgga cgcaagaaaa                                               20

<210> SEQ ID NO 16
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
agccaccaga gcttttgaga                                               20

<210> SEQ ID NO 17
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
cgacctggaa gtccaactac                                               20

<210> SEQ ID NO 18
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
atctgctgca tctgcttg                                                 18
```